(12) United States Patent
Xi et al.

(10) Patent No.: US 10,668,090 B2
(45) Date of Patent: Jun. 2, 2020

(54) LIVER SPECIFIC DELIVERY-BASED ANTIVIRAL PRODRUG NUCLEOSIDE CYCLOPHOSPHATE COMPOUND AND USES THEREOF

(71) Applicant: ZHEJIANG PALO ALTO PHARMACEUTICALS, INC, Quzhou, Zhejiang (CN)

(72) Inventors: Zhijian Xi, Zhejiang (CN); Huaqiang Xu, Zhejiang (CN); Chunping Lu, Zhejiang (CN); Zhongshan Wu, Zhejiang (CN); Feng Sun, Zhejiang (CN); Zhenwei Zhang, Zhejiang (CN)

(73) Assignee: ZHEJIANG PALO ALTO PHARMACEUTICALS, INC, Quzhou (CN)

( * ) Notice: Subject to any disclaimer, the term of this patent is extended or adjusted under 35 U.S.C. 154(b) by 0 days.

(21) Appl. No.: 16/231,497

(22) Filed: Dec. 22, 2018

(65) Prior Publication Data
US 2019/0125771 A1    May 2, 2019

Related U.S. Application Data

(63) Continuation of application No. PCT/CN2017/089850, filed on Jun. 23, 2017.

(30) Foreign Application Priority Data

Jun. 24, 2016 (CN) .......................... 2016 1 0492624
Apr. 18, 2017 (CN) .......................... 2017 1 0254377

(51) Int. Cl.
| | | |
|---|---|---|
| A61K 31/675 | (2006.01) | |
| A61P 31/20 | (2006.01) | |
| A61P 31/18 | (2006.01) | |
| A61P 31/14 | (2006.01) | |
| A61K 31/662 | (2006.01) | |
| C07F 9/6571 | (2006.01) | |

(52) U.S. Cl.
CPC .......... *A61K 31/675* (2013.01); *A61K 31/662* (2013.01); *A61P 31/14* (2018.01); *A61P 31/18* (2018.01); *A61P 31/20* (2018.01); *C07F 9/657181* (2013.01)

(58) Field of Classification Search
CPC ................................................. C07F 9/657181
See application file for complete search history.

(56) References Cited

U.S. PATENT DOCUMENTS

2002/0052345 A1    5/2002    Erion et al.

FOREIGN PATENT DOCUMENTS

| CN | 101475594 A | 7/2009 |
|---|---|---|
| CN | 103333209 A | 10/2013 |
| CN | 104710477 A | 6/2015 |
| CN | 201610492624.9 | * 6/2016 |
| CN | 201710254377.3 | * 4/2017 |
| WO | 2004037161 A2 | 5/2004 |

OTHER PUBLICATIONS

CN 101475594, pp. 1-5, translation from WIPO website, Sep. 2, 2019.*
Fisher et al. (AIDS, (2001), vol. 15(13), pp. 1695-1700) (Year: 2001).*
Reddy,K.Raja et al.,"Pradefovir: A Prodrug That Targets Adefovir to the Liver for the Treatment of Hepatitis B", Journal of Medicinal Chemisttry, vol. 51, No. 3, Jan. 4, 2008.

* cited by examiner

*Primary Examiner* — Susanna Moore
(74) *Attorney, Agent, or Firm* — Wayne & Ken, LLC; Tony Hom

(57) ABSTRACT

Disclosed are a liver specific delivery (LSD)-based antiviral prodrug nucleoside cyclophosphate compound and uses thereof, and in particular, provided are a compound of formula (I), and an isomer, a pharmaceutically acceptable salt, a hydrate and a solvate thereof, and the corresponding pharmaceutical composition. The present invention also provides uses of the present compounds, alone or in combination with other antiviral drugs, in the treatment of the diseases caused by hepatitis B virus (HBV), hepatitis D virus (HDV) and human immunodeficiency virus (HIV).

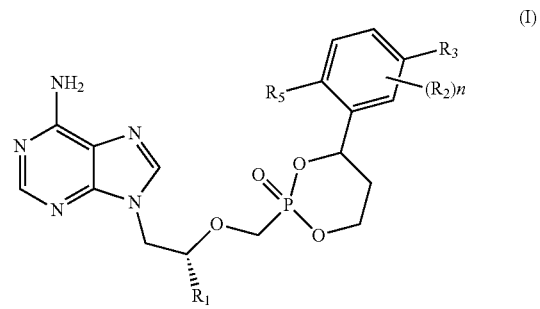

(I)

4 Claims, 4 Drawing Sheets

LIVER SPECIFIC DELIVERY-BASED ANTIVIRAL PRODRUG NUCLEOSIDE CYCLOPHOSPHATE COMPOUND AND USES THEREOF

CROSS-REFERENCE TO RELATED APPLICATIONS

This application is a continuation of International Patent Application No. PCT/CN2017/089850, filed on Jun. 23, 2017 which claims the benefit of priority from Chinese Application No. 201610492624.9, filed on Jun. 24, 2016 and Chinese Application No. 201710254377.3, filed on Apr. 18, 2017. The contents of the aforementioned applications, including any intervening amendments thereto, are incorporated herein by reference.

TECHNICAL FIELD

The present invention relates to a liver specific delivery-based antiviral prodrug nucleoside cyclophosphate compound or an optical isomer, a hydrate, a solvate, a pharmaceutically acceptable salt or a pharmaceutical composition thereof, and uses thereof.

BACKGROUND

Viruses such as hepatitis B virus (HBV), hepatitis D virus (HDV), human immunodeficiency virus (HIV) are greatest threats to human health. For example, viral hepatitis B (hepatitis B) is caused by hepatitis B virus and mainly in the form of inflammatory lesions of the liver, leading to damage to multiple organs. World Health Organization (WTO) survey results show that there are 240 million cases infected with chronic hepatitis B and 780,000 cases died each year from hepatitis B, where 650,000 cases die from cirrhosis and liver cancer caused by chronic hepatitis B and 130,000 cases die from acute hepatitis B. Hepatitis B has been an critical and global issue for health.

Anti-HBV drugs generally include a class of nucleotide drugs such as adefovir dipivoxil, tenofovir disoproxil fumarate (TDF), tenofovir alafenamide (TAF), entecavir, lamivudine and telbivudine. These drugs act through activation into a triphosphate metabolite in cells to inhibit the DNA or RNA polymerase activity of the virus, thus preventing the synthesis of DNA or RNA and inhibiting viral replication.

Some nucleotide compounds, such as adefovir, tenofovir, etc., are highly electronegative at physiological pH and thus have poor transmembrane ability and low bioavailability for oral administration. Meanwhile, oral administration of such compounds may increase toxic effect to gastrointestinal tract and kidney. However, the nucleotide compounds can be esterified to form ester prodrugs such as adefovir dipivoxil and tenofovir disoproxil fumarate, improving the bioavailability and tissue distribution. However, before being taken up by hepatocytes, most of the ester prodrugs may be hydrolyzed to electronegative bioactive components (such as adefovir and tenofovir) by the ester hydrolase which is widely distributed in the body. Such components do not easily enter the hepatocytes, but are actively transported and absorbed by the renal proximal tubule causing nephrotoxicity.

Structure of the cyclophosphate (4-aryl-2-oxo-1,3,2-dioxaphosphorinane) precursor ensures excellent liver-specific delivery performance and its mechanism is very clear. As shown in FIG. 1, 4-aryl-substituted position is specifically catalyzed by CYP3A of cytochrome P450 isozyme family in hepatocytes to give a hydroxyl group followed by ring-opening to form an electronegative phosphate intermediate. This intermediate is maintained within the cell due to the difficulty in passing through the cell membrane. The electronegative phosphate intermediate is hydrolyzed and β-eliminated to form a nucleoside monophosphate compound under catalysis of phosphodiesterase. The nucleoside monophosphate compound is then catalyzed by nucleotide kinases to form a bioactive nucleotide triphosphate compound. At the same time, a metabolic by-product aryl vinyl ketone is removed by 1,4-addition reaction with glutathione, which is abundant in hepatocytes and has antioxidation and free radical-scavenging activity. In addition, the addition product has not been reported to have side effects.

Using adefovir as an active component, it is found that through modification of substituents on the aryl group, for example mono-substitution, disubstitution, a compound substituted with chloride at a meta-position on the aromatic ring, i.e., pradefovir, is metabolized to adefovir in the presence of CYP3A enzyme at a highest metabolism rate, nearly 5 times that of the compound substituted with chloride at 3- and 5-positions on the aromatic ring (US200707214668 B2).

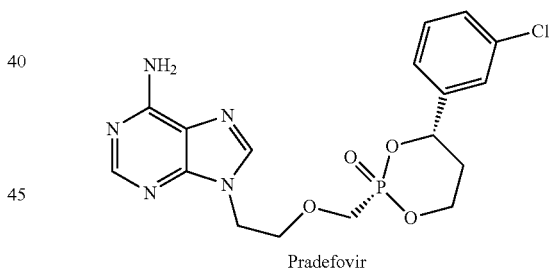

Pradefovir

However, there is still a lack of a viral inhibitory compounds with high activity, strong liver delivery specificity, and low toxic and side effects. Therefore, there is a need in the art to develop a novel antiviral compound with high activity, strong liver delivery specificity and low toxic and side effects.

SUMMARY

The present invention synthesizes a cyclophosphate of an antiviral nucleotide drug, and further modifies substituents on its aromatic ring to produce a class of prodrugs capable of liver-specific delivery (LSD) and with higher efficacy and less toxic and side effects.

In a first aspect, the present invention provides a compound of formula (II), or an optical isomer thereof, a pharmaceutically acceptable salt, a hydrate or a solvate thereof:

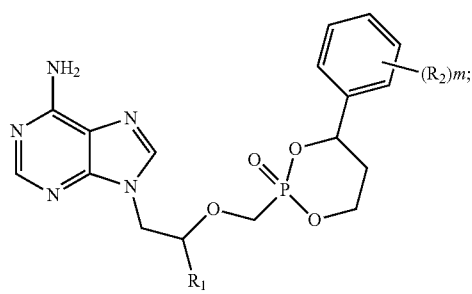

(II)

wherein:

R₁ is selected from the group consisting of hydrogen, amino, substituted or unsubstituted $C_1$-$C_6$ alkyl, substituted or unsubstituted $C_3$-$C_8$ cycloalkyl, substituted or unsubstituted $C_1$-$C_6$ alkoxy group and substituted or unsubstituted $C_1$-$C_6$ alkylamino; where substitution comprises one or more substituents selected from the group consisting of halogen, $C_1$-$C_3$ alkyl, $C_1$-$C_3$ haloalkyl, nitro, hydroxyl, amino and cyano group;

m is 0, 1, 2, 3, 4 or 5;

each R₂ is independently selected from the group consisting of halogen, nitro, hydroxyl, amino, cyano group, substituted or unsubstituted $C_1$-$C_6$ alkyl, substituted or unsubstituted $C_3$-$C_8$ cycloalkyl, substituted or unsubstituted $C_1$-$C_6$ alkoxy group, substituted or unsubstituted $C_3$-$C_6$ alkylamino, substituted or unsubstituted $C_1$-$C_6$ carboxyl, substituted or unsubstituted $C_1$-$C_6$ ester group, substituted or unsubstituted $C_2$-$C_6$ alkanoyl and substituted or unsubstituted $C_2$-$C_6$ alkylamide group;

where substitution comprises one or more substituents selected from the group consisting of halogen, $C_1$-$C_3$ alkyl, $C_1$-$C_3$ haloalkyl, nitro, hydroxyl, amino and cyano group; and each chiral center in formula (II) is R- or S-configuration.

In another preferred embodiment, P2 and 4-positioned aryl in the cyclophosphate structure are cis in relation to each other, and P2 is R-configuration and C₄ is S-configuration.

In another preferred embodiment, R₁ is selected from the group consisting of H, $C_1$-$C_3$ alkyl and cyclopropyl.

In another preferred embodiment, R₁ is selected from the group consisting of H, methyl and cyclopropyl.

In another preferred embodiment,

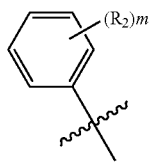

is selected from the group consisting of:

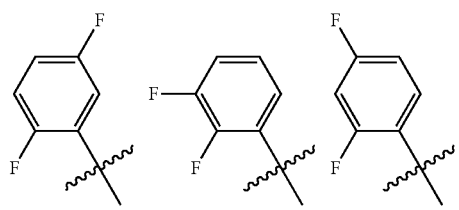

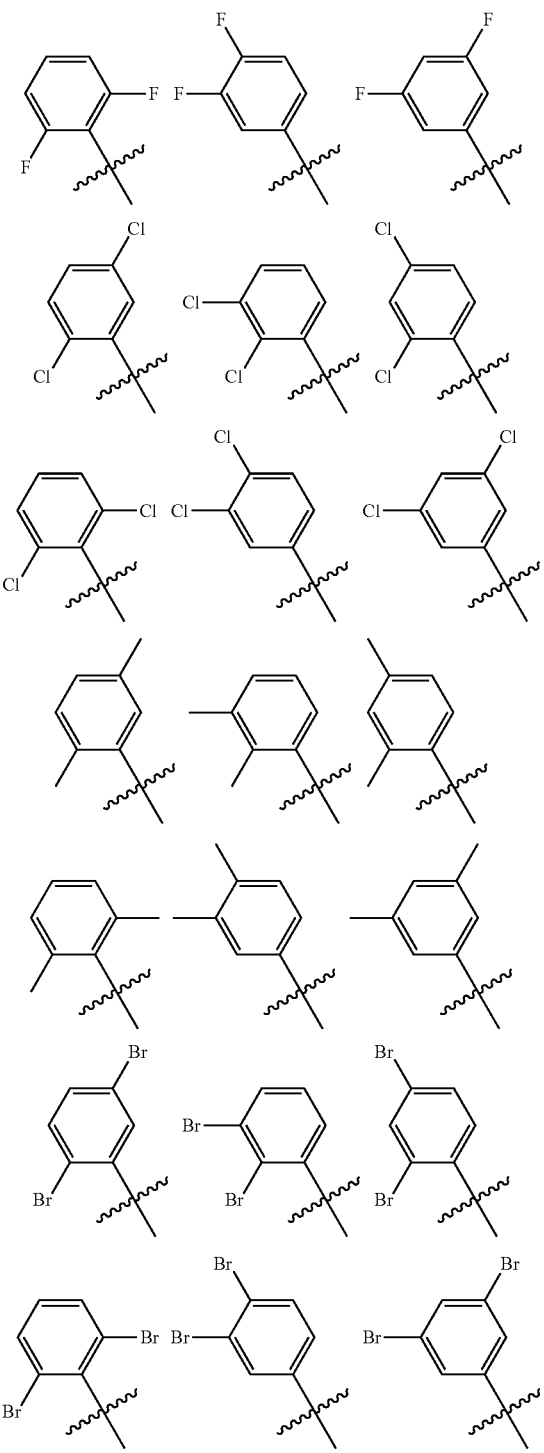

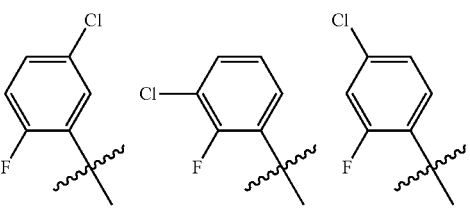

-continued
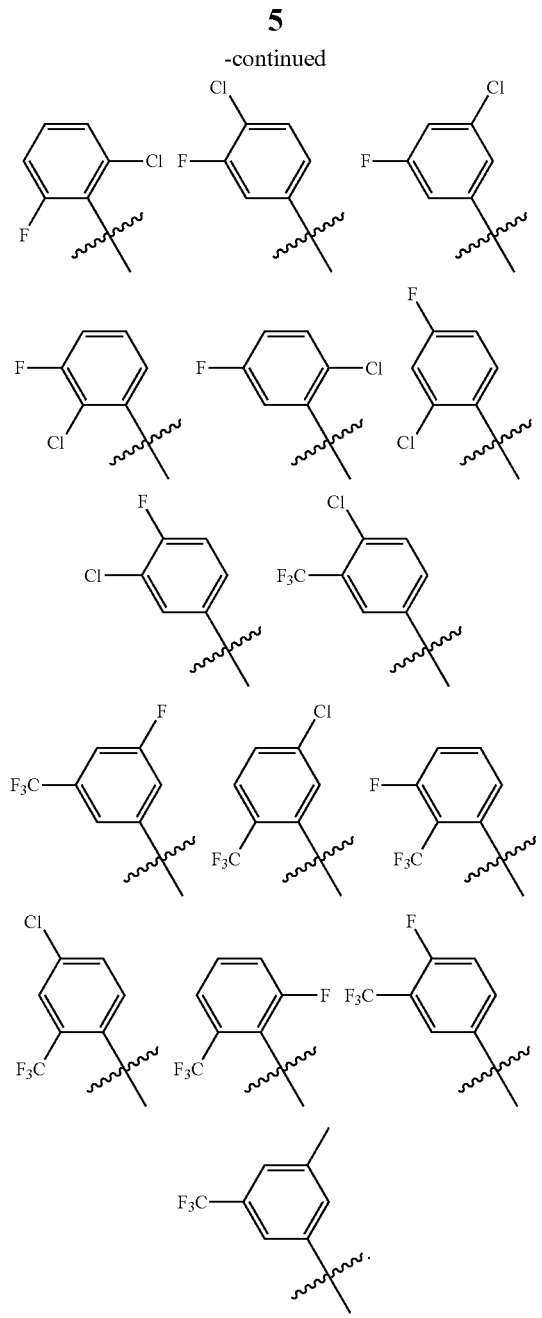
In another preferred embodiment, the compound is selected from the group consisting of:
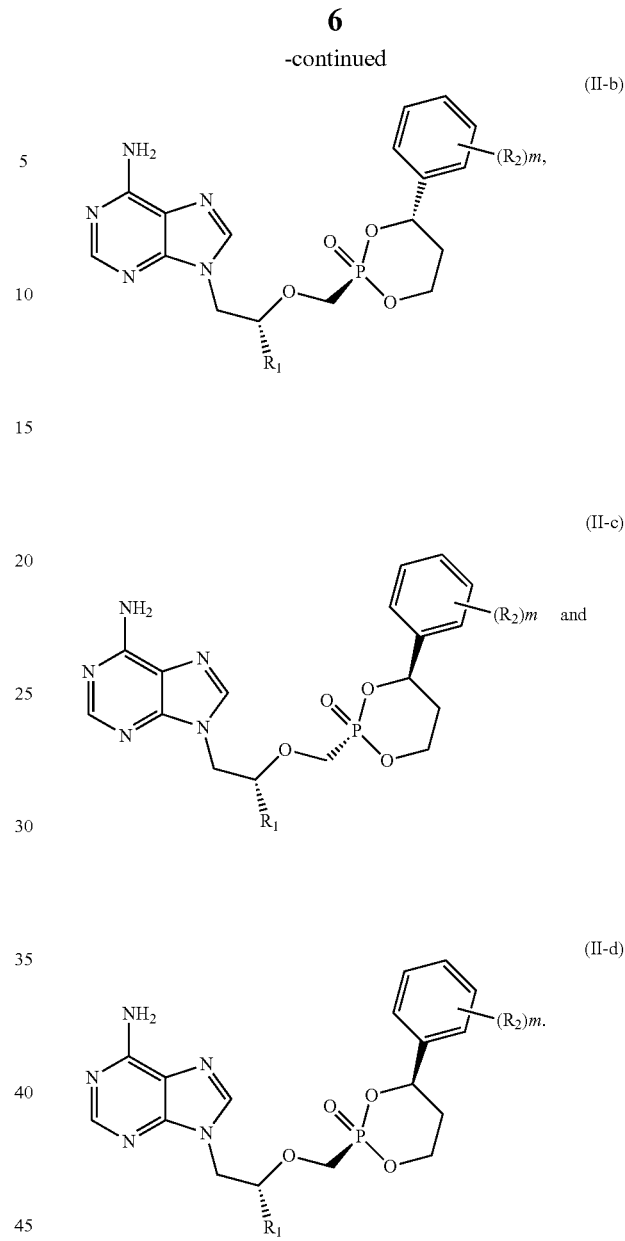
In another preferred embodiment, the compound of formula (II) is a compound of formula (II-a).
In another preferred embodiment, the compound has a structural formula shown as follows:
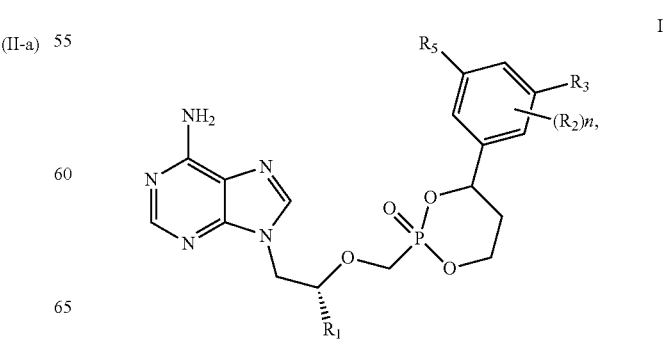

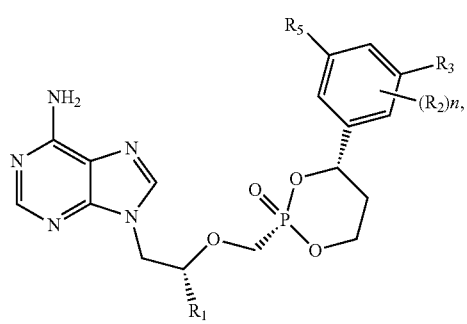

I-a

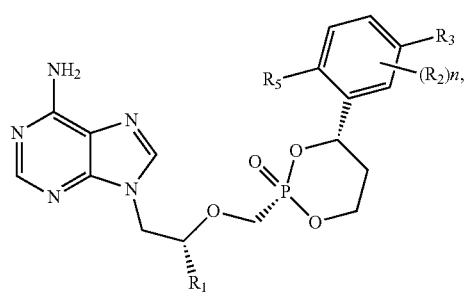

III-a

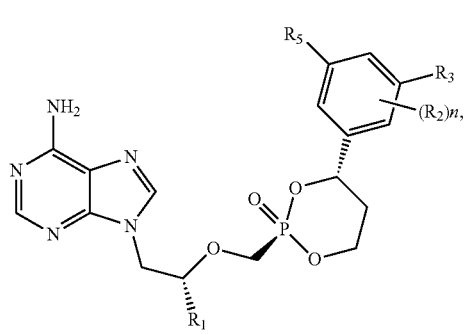

I-b

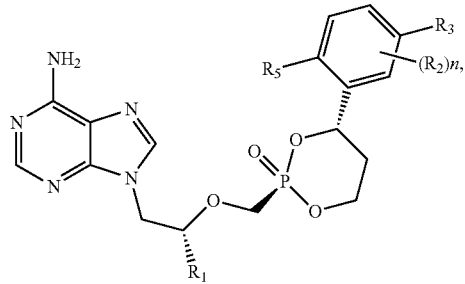

III-b

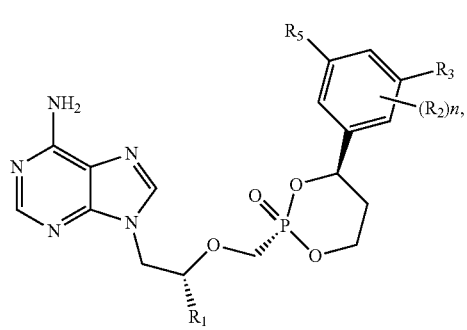

I-c

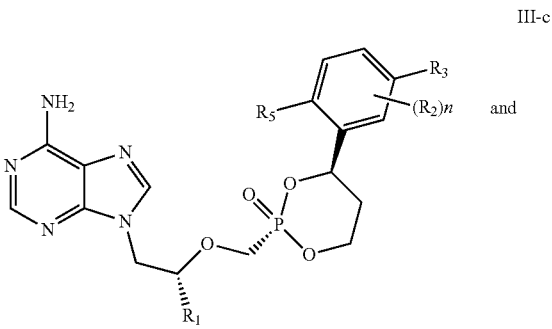

III-c and

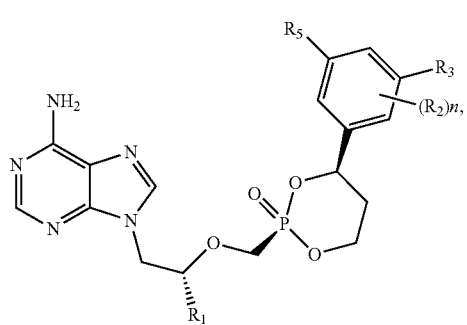

I-d

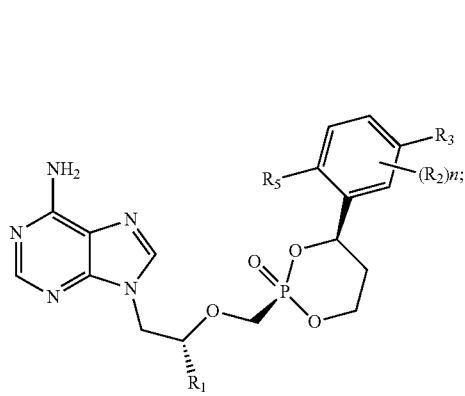

III-d

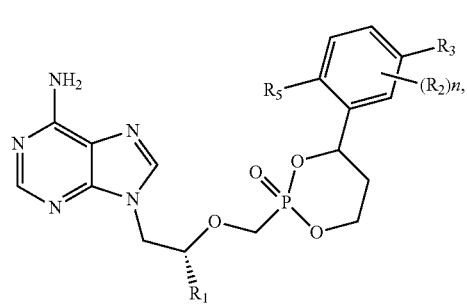

III wherein $R_3$ and $R_5$ are independently halogen; and
n is 0, 1, 2 or 3.

In another preferred embodiment, the compound is a compound of formula (I-a) or (III-a).

In another preferred embodiment, $R_3$ is halogen, $R_5$ is F, Br or I, and $R_3 \neq R_5$.

In another preferred embodiment, $R_3$ is Cl, and $R_5$ is F.

In another preferred embodiment, the compound is selected from the group consisting of:

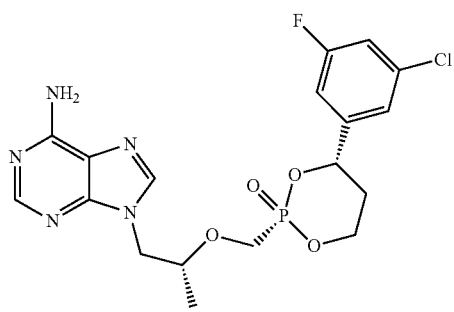

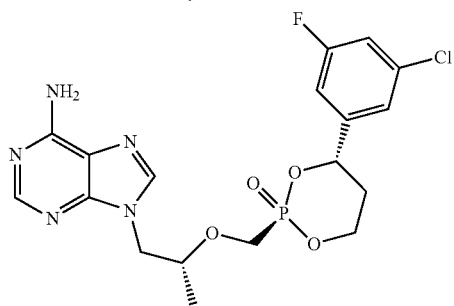

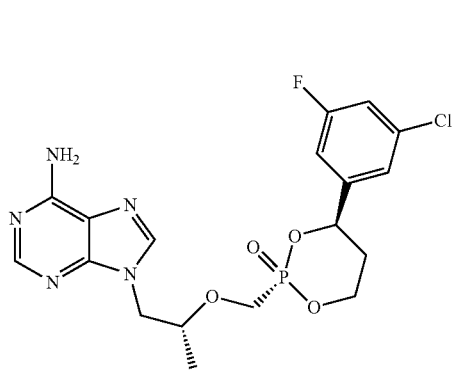

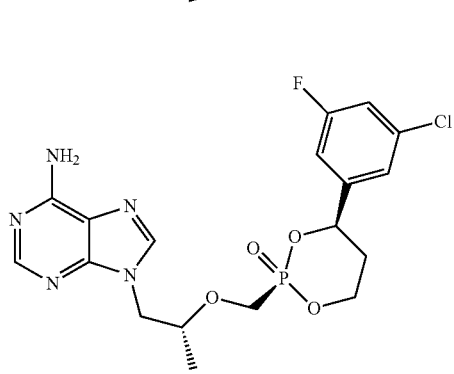

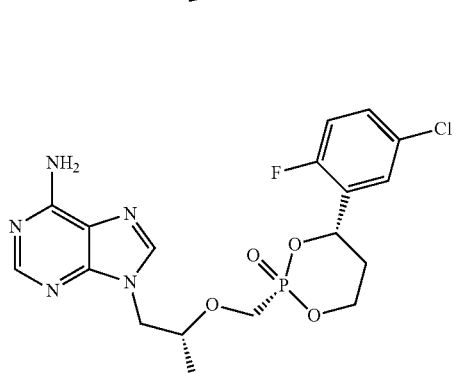

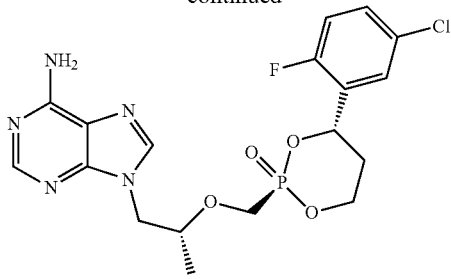

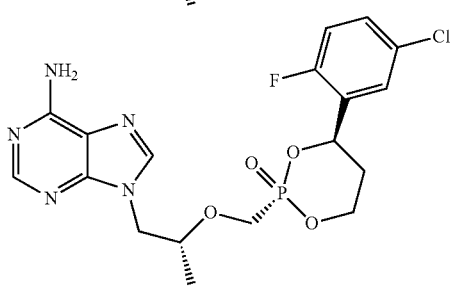

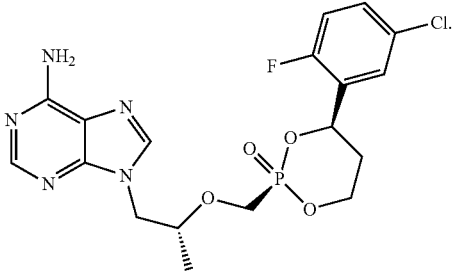

In another preferred embodiment, a salt of the compound is a pharmaceutically acceptable salt formed from the compound of formula (I), (II) or (III) and an inorganic or organic acid, or formed from the compound of formula (I), (II) or (III) and a base; and the compound of formula (I), (II) or (III) or a salt thereof is amorphous or crystalline.

In a second aspect, the present invention provides a pharmaceutical composition comprising a therapeutically effective amount of the compound according to the first aspect of the present invention or an optical isomer, a pharmaceutically acceptable salt, a hydrate or a solvate thereof, and a pharmaceutically acceptable auxiliary, diluent or carrier.

In a third aspect, the present invention provides use of the compound or an optical isomer, a pharmaceutically acceptable salt, a hydrate or a solvate thereof according to the first aspect of the invention, or the pharmaceutical composition according to the second aspect of the invention, for the manufacture of a pharmaceutical composition for treating and or preventing an acute or chronic disease associated with hepatitis B virus (HBV), hepatitis D virus (HDV) or human immunodeficiency virus (HIV) infection.

In another preferred embodiment, the acute or chronic disease associated with hepatitis B virus (HBV), hepatitis D virus (HDV) or human immunodeficiency virus (HIV) infection is selected from the group consisting of hepatitis B, hepatitis D or acquired immune deficiency syndrome (AIDS).

In a fourth aspect, the present invention provides a method of preparing the compound of formula (II) according to the first aspect of the invention, which includes the step of:

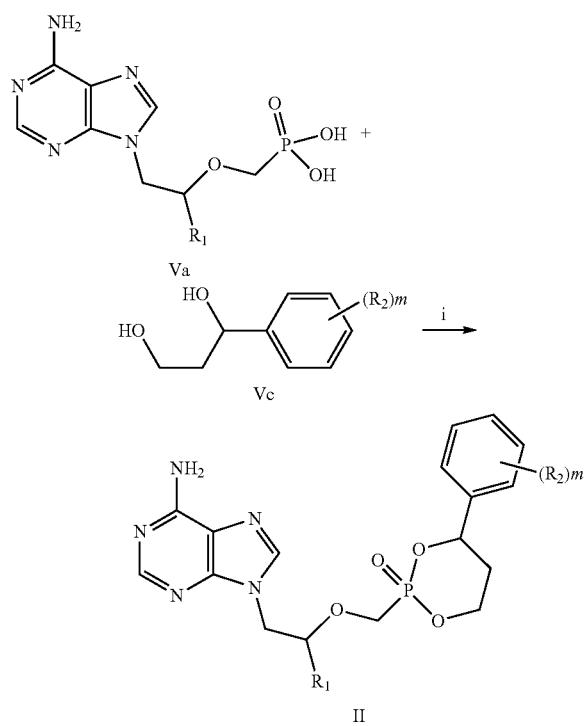

(i) condensing a compound of formula (Va) and a compound of formula (Vc) in an inert solvent to produce the compound of formula (II).

In another preferred embodiment, in step (i) the reaction is carried out in the presence of a condensing agent.

In another preferred embodiment, the condensing agent is dicyclohexylcarbodiimide (DCC).

In another preferred embodiment, the condensation reaction is carried out at 60-100° C. (about 80° C.).

In another preferred embodiment, the time of the condensation reaction is 1-72 hours, preferably 3-48 hours, and more preferably 6-24 hours.

In another preferred embodiment, the inert solvent is selected from the group consisting of N,N-dimethylformamide, pyridine or combination thereof, preferably a solvent mixture of N,N-dimethylformamide and pyridine at a volume ratio (v/v) of 20:1 to 1:5 (more preferably, 10:1 to 1:2 (v/v)).

In another preferred embodiment, the compound of formula (Vc) (preferably a chiral 1,3-propanediol derivative) is prepared by the following method including steps of:

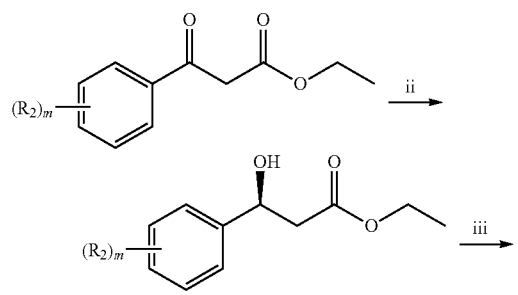

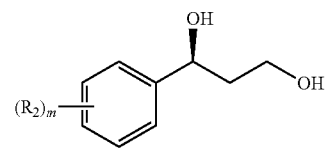

(ii) reducing

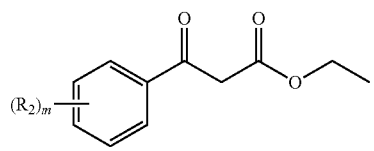

at 40-80° C. (for example, for 1-5 hours) in the presence of HCOOH, Et₃N and (S,S)—N-(p-Toluenesulfonyl)-1,2-diphenylethanediamine(chloro)(p-cymene)ruthenim(II) in an inert solvent (for example, DMF) to produce

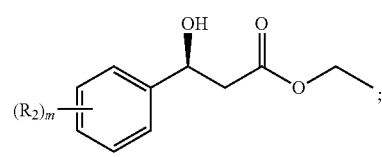

and (iii) reacting a reductant (for example, NaBH₄) with

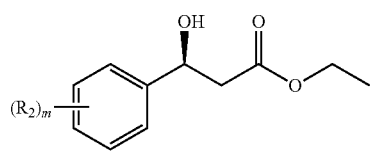

(for example, for 1-5 hours) in an amphoteric solvent (for example, EtOH) to produce

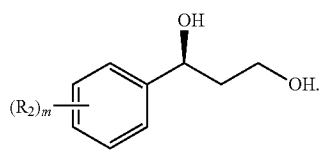

In another preferred embodiment,

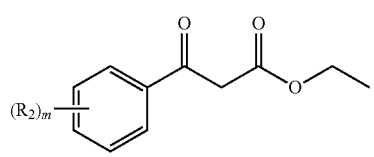

is prepared using any one of methods 1-3.

Method 1

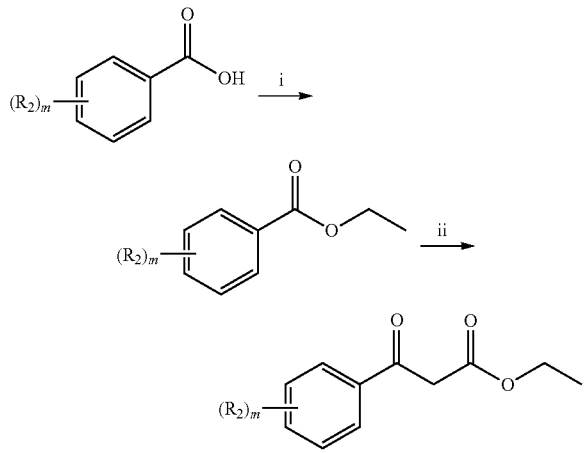

(i) reacting $SOCl_2$ with

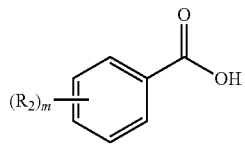

in an amphoteric solvent (for example, EtOH) to produce

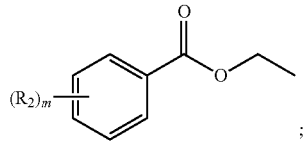

and (ii) reacting ethyl acetate with

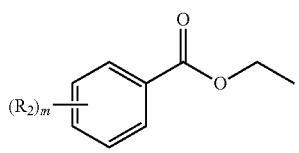

at −60 to −20° C. in the presence of a base (for example, LiHMDS) in an inert solvent (for example, THF) (for example, for 10-30 minutes) to produce

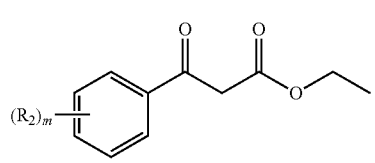

Method 2

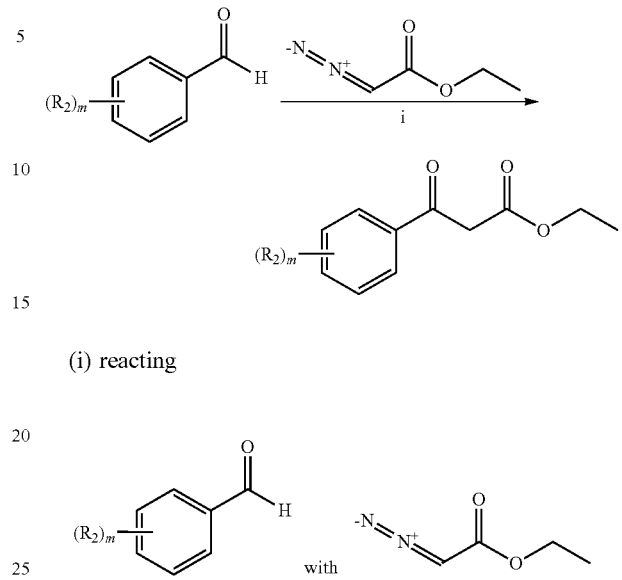

(i) reacting

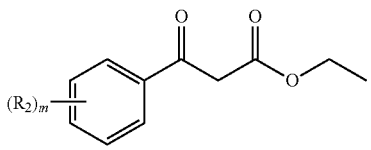 with at room temperature in the presence of $SnCl_2$ in an inert solvent (for example, DCM) to produce

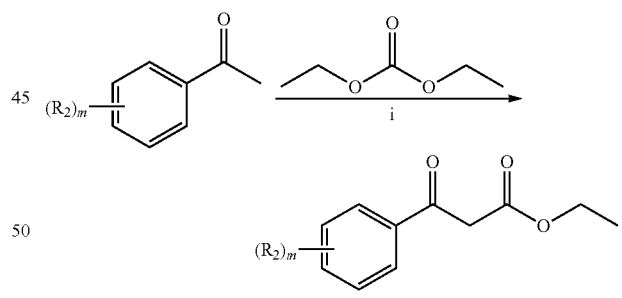

Method 3

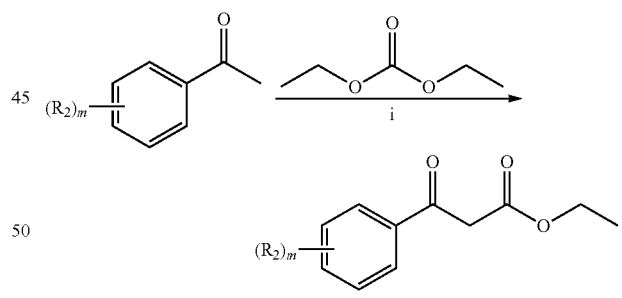

(i) reacting

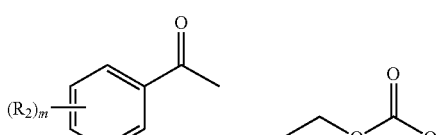 with at a reflux temperature overnight in the presence of a base (for example, potassium t-butoxide) in an inert solvent (for example, THF) to produce

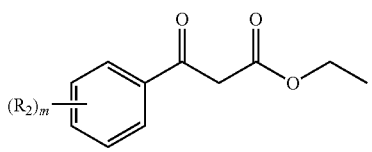

It should be understood that various technical features described above and various technical features described hereinafter (for example, in embodiments) of the present invention can be combined with each other to constitute a new or preferred technical solution that will not be described here due to pages of this application.

NOTES

Figure 1:
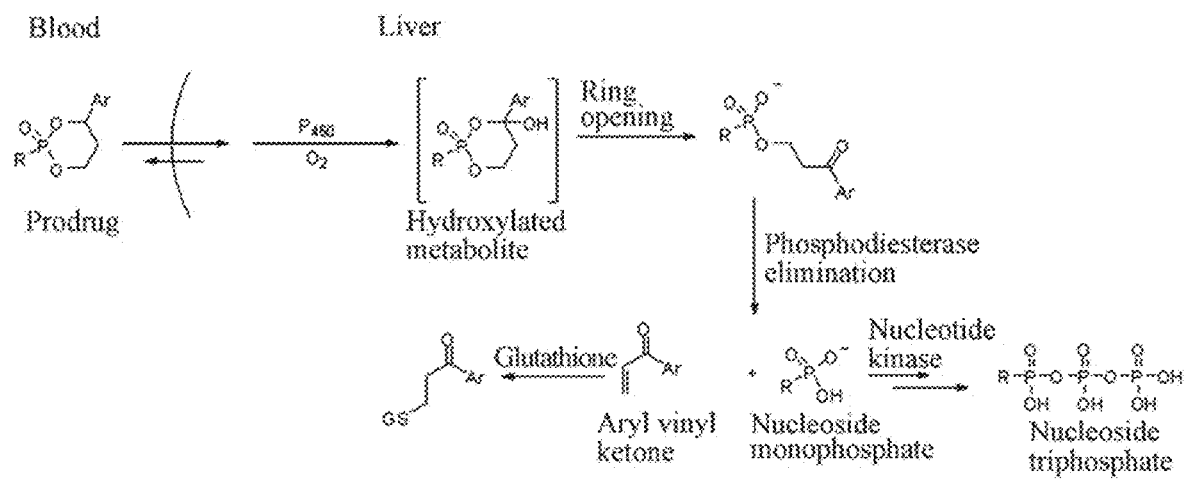
FIG. 1 is a schematic diagram showing the action mechanism of a liver-specific delivery-based compound.

PMPA: (R)-9-(2-methoxypropyl phosphate)-adenine
PMEA: 9-[2-(phosphonomethoxy) ethyl]adenine
S-configuration cis, unless otherwise specified, means that C4 on a phosphate ring is S-configuration, and P2 and 4-positioned aryl group are cis in relation to each other.

DETAILED DESCRIPTION OF EMBODIMENTS

Through a long-term and in-depth research, the inventor has surprisingly found, after a screening and investigation of a large number of compounds, that a class of compounds of specific structural formula (I) or formula (III) (for example, with different halogens at 3 and 5 positions on the benzene ring, or different halogens at 2 and 5 positions on the benzene ring) have excellent antiviral activity, significantly improved liver-specific delivery and significantly reduced toxic and side effects.

Terminology

As used herein, term "$C_1$-$C_6$ alkyl" refers to a straight or branched alkyl having 1 to 6 carbon atoms, such as methyl, ethyl, propyl, isopropyl, butyl, isobutyl, sec-butyl, tert-butyl, or the like.

As used herein, term "$C_2$-$C_6$ alkanoyl" refers to a substituent of a straight or branched alkyl-carbonyl structure having 1 to 6 carbon atoms, such as acetyl, propionyl, butyryl, or the like.

As used herein, term "$C_1$-$C_6$ alkylamino" refers to a substituent of a straight or branched alkyl-amino structure having 1 to 6 carbon atoms, such as methylamino, dimethylamino, ethylamino, propylamino, diethylamino, or the like.

As used herein, term "halogen" refers to F, Cl, Br and I.

As used herein, term "containing", "comprising" or "including" indicates that various ingredients may be used together in the mixture or composition of the invention. Therefore, terms "mainly consisting of" and "consisting of" are included in the term "containing".

As used herein, term "pharmaceutically acceptable ingredient" refers to a substance which is suitable for humans and/or animals without excessive adverse side effects such as toxicity, irritation and allergic, that is, a substance with a reasonable ratio of benefit to risk.

As used herein, term "effective amount" refers to an amount at which a therapeutic agent used can treat, alleviate or prevent a target disease or condition or an amount at which a therapeutic agent used can exhibit a detectable therapeutic or prophylactic effect. A precise effective amount to a subject depends on the size and health of the subject, the nature and extent of the symptom and the selected therapeutic agent and/or combination of therapeutic agents. Therefore, it is useless to specify a precise effective amount in advance. However, for some specific conditions, a clinician is able to determine the effective amount through conventional experiment.

Unless otherwise specified, term "substitution" used herein means that one or more hydrogen atoms on a group are substituted with substituents selected from the group consisting of halogen, $C_1$-$C_3$ alkyl, $C_1$-$C_3$ haloalkyl, nitro, hydroxyl, amino and cyano group.

Unless otherwise specified, all compounds appearing in the present invention are intended to include all possible optical isomers, such as single chiral compounds, or a mixture of various chiral compounds (i.e., racemates). Among all the compounds of the present invention, each of the chiral carbon atoms may be optionally R or S configuration, or a mixture thereof.

As used herein, term "compound of the present invention" refers to a compound of formula (II). Such term further includes various crystal forms, pharmaceutically acceptable salts, hydrates or solvates of the compound of formula (II).

As used herein, term "pharmaceutically acceptable salt" refers to a salt formed by the compound of the invention with an acid or base and suitable for use as a medicine. The pharmaceutically acceptable salts include inorganic and organic salts. A preferred class of salts is formed by the compound of the invention with an acid. The acids suitable for forming the salts include but are not limited to: inorganic acids such as hydrochloric acid, hydrobromic acid, hydrofluoric acid, sulfuric acid, nitric acid and phosphoric acid, organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, phenylmethanesulfonic acid and benzenesulfonic acid, and acidic amino acids such as aspartic acid and glutamic acid.

Some of the compounds of the invention may be crystallized or recrystallized with water or various organic solvents, where various solvates may be formed. The solvates of the present invention include stoichiometric solvates such as hydrates and compounds containing variable amounts of crystal water formed upon the preparation using lyophilization.

It should be understood that various thermodynamically stable isomers may be present after preparation of the compounds of the invention, such as a tautomer, a conformer, a meso compound, and an enantiomer or a diastereomer. Such variations will be apparent for those skilled in the art after reading the present invention.

Compound of Formula (I) or (III) and Preparation Thereof

In order to provide a highly effective and low toxic prodrug which can ensure a concentrated release of the antiviral nucleotide drug in hepatocytes through a liver-specific delivery-based mechanism, the inventor prepared a preferred compound of formula (II), that is, a compound of formula (I) or (III)

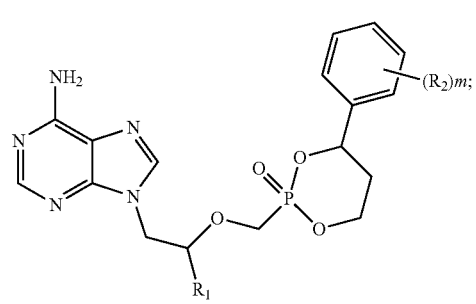

(II)

wherein:

$R_1$ is selected from the group consisting of hydrogen, amino, substituted or unsubstituted $C_1$-$C_6$ alkyl, substituted or unsubstituted $C_3$-$C_8$ cycloalkyl, substituted or unsubstituted $C_1$-$C_6$ alkoxy group and substituted or unsubstituted $C_1$-$C_6$ alkylamino; where substitution comprises one or more substituents selected from the group consisting of halogen, $C_1$-$C_3$ alkyl, $C_1$-$C_3$ haloalkyl, nitro, hydroxyl, amino and cyano group;

m is 0, 1, 2, 3, 4 or 5;

each $R_2$ is independently selected from the group consisting of halogen, nitro, hydroxyl, amino, cyano group, substituted or unsubstituted $C_1$-$C_6$ alkyl, substituted or unsubstituted $C_3$-$C_8$ cycloalkyl, substituted or unsubstituted $C_1$-$C_6$ alkoxy group, substituted or unsubstituted $C_1$-$C_6$ alkylamino, substituted or unsubstituted $C_1$-$C_6$ carboxyl, substituted or unsubstituted $C_1$-$C_6$ ester group, substituted or unsubstituted $C_2$-$C_6$ alkanoyl and substituted or unsubstituted $C_2$-$C_6$ alkylamide group;

where substitution comprises one or more substituents selected from the group consisting of halogen, $C_1$-$C_3$ alkyl, $C_1$-$C_3$ haloalkyl, nitro, hydroxyl, amino and cyano group; and each chiral center in formula (II) is R- or S-configuration.

In a preferred embodiment,

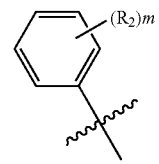

is selected from the group consisting of:

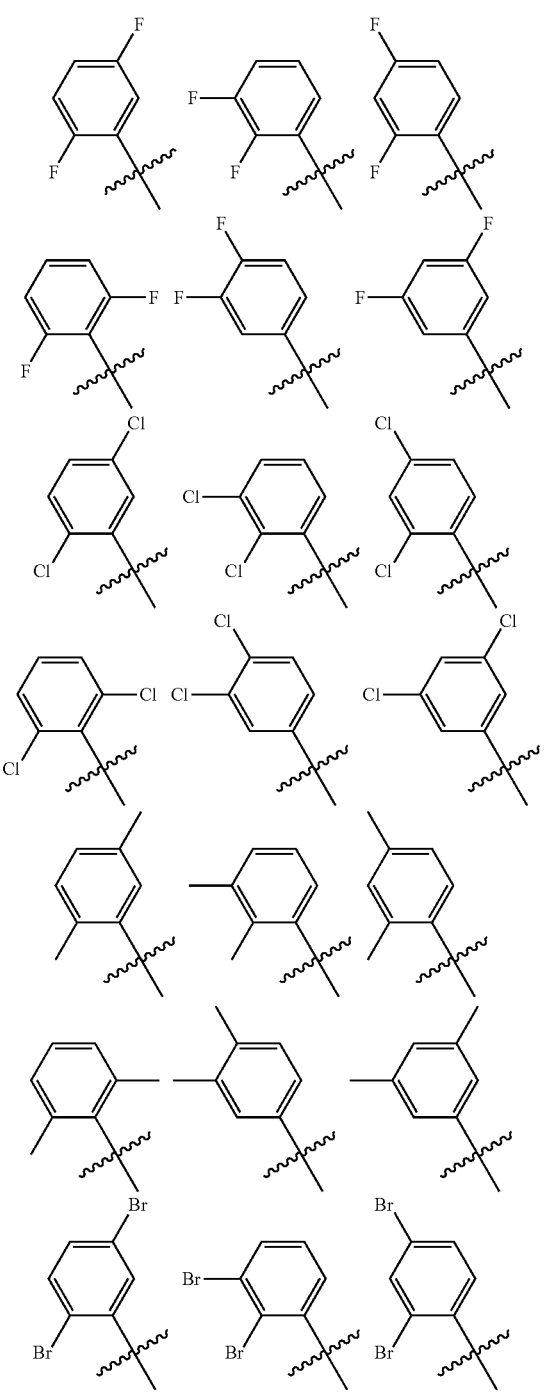

-continued
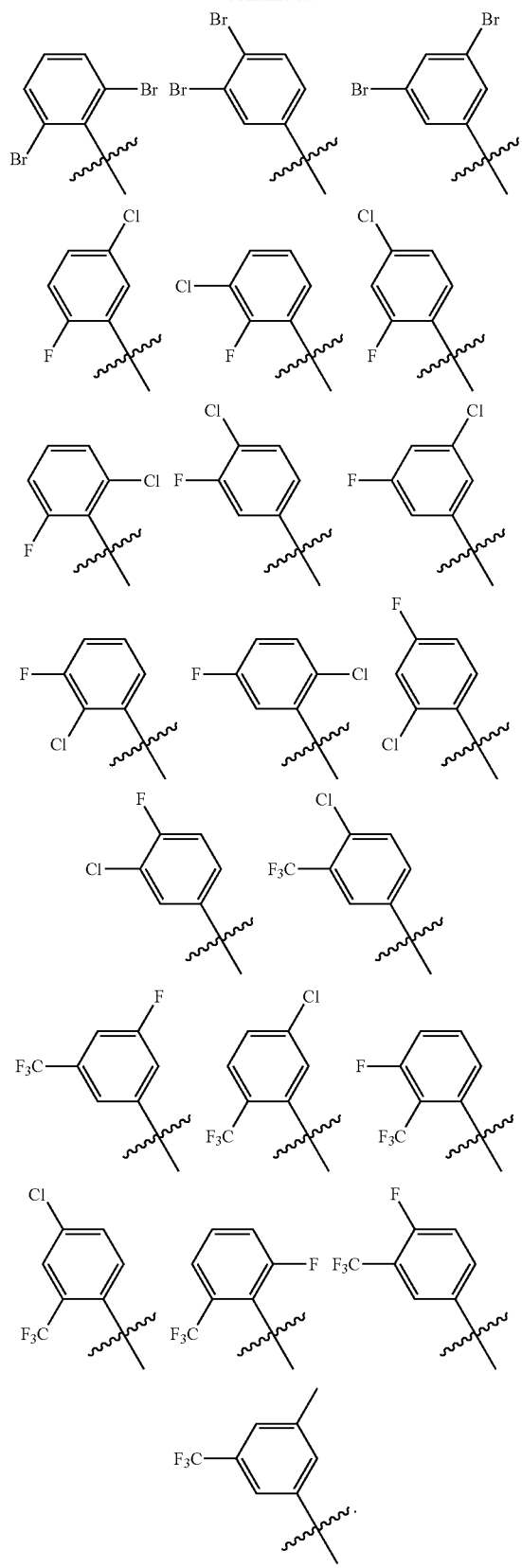
A preferred class of compounds of formula (II) has a structural formula shown as follows:
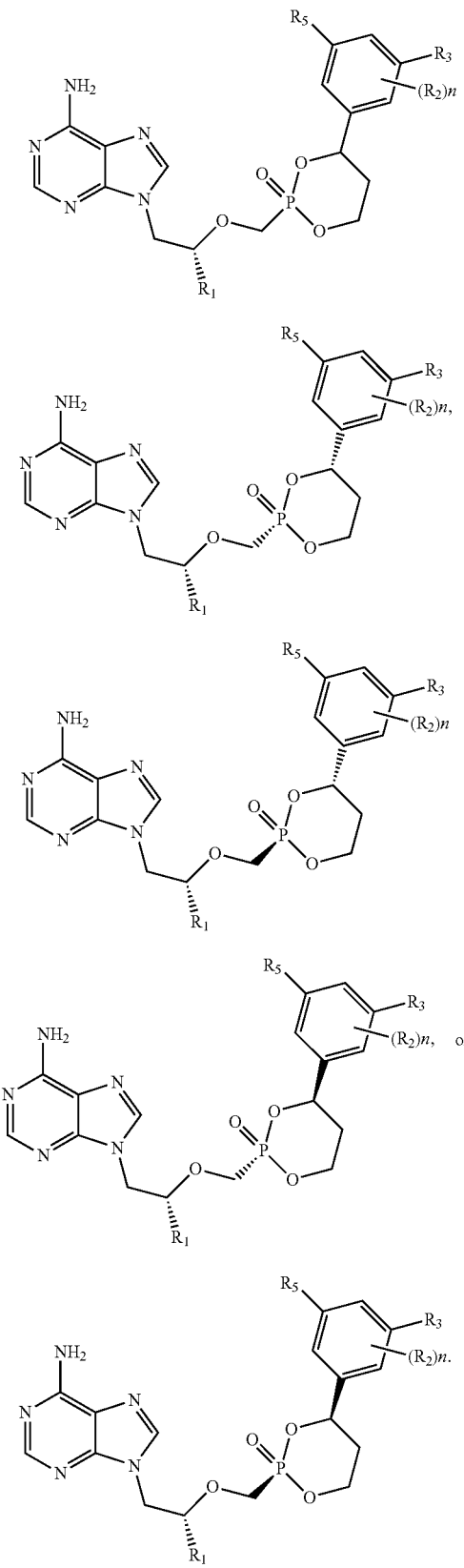
In another preferred embodiment, the compound of formula (I) is a compound of formula (I-a).

In another preferred embodiment, P2 and 4-positioned aryl in the cyclophosphate structure are cis in relation to each other, and P2 is R-configuration and C4 is S-configuration.

In another preferred embodiment, R₁ is selected from the group consisting of H, C₁-C₃ alkyl and cyclopropyl.

In another preferred embodiment, R₁ is selected from the group consisting of H, methyl and cyclopropyl.

More preferably, R₃ is Cl and R₅ is F; or R₃ is Cl and R₅ is Br; or R₃ is Cl and R₅ is Cl.

In another preferred embodiment, the optical isomer includes a tautomer, a cis or trans isomer, a conformer, a meso compound, and an enantiomer or a diastereomer.

In another preferred embodiment, the compound is selected from the group consisting of:

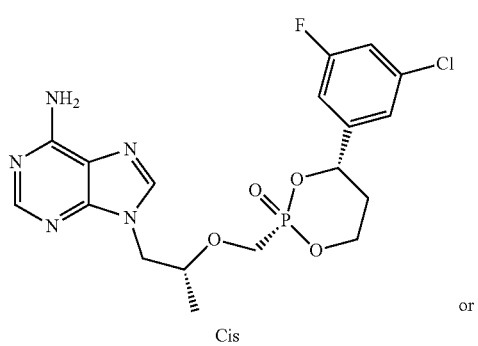

Cis or

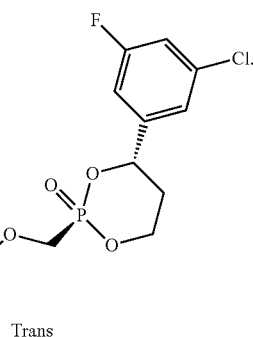

Trans

Another preferred class of compounds of formula (II) has a structural formula (III) shown as follows:

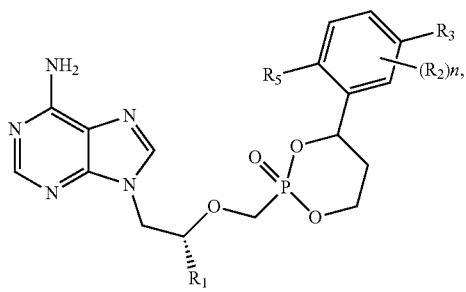

III

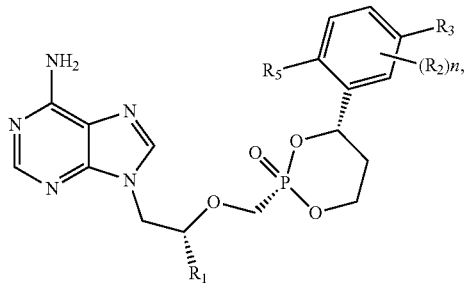

III-a

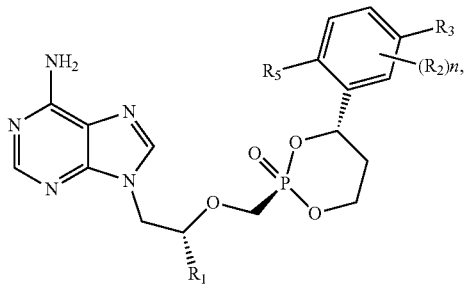

III-b

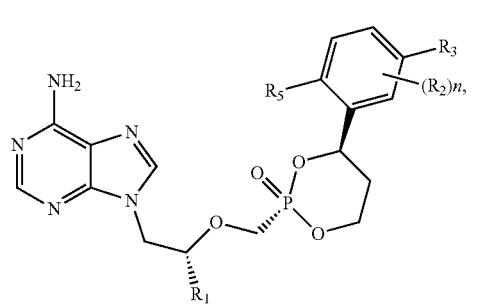

III-c or

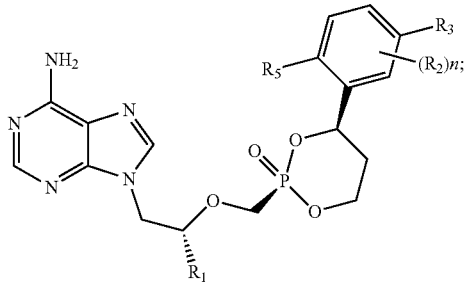

III-d wherein, each group is defined as above.

In another preferred embodiment, the compound of formula (III) is a compound of formula (III-a).

In another preferred embodiment, P2 and 4-positioned aryl in the cyclophosphate structure are cis in relation to each other, and P2 is R-configuration and C4 is S-configuration.

In another preferred embodiment, R₁ is selected from the group consisting of H, C₁-C₃ alkyl and cyclopropyl.

In another preferred embodiment, R₁ is selected from the group consisting of H, methyl and cyclopropyl.

More preferably, R₃ is Cl and R₅ is F; or R₃ is Cl and R₅ is Br; or R₃ is Cl and R₅ is Cl.

In another preferred embodiment, the optical isomer includes a tautomer, a cis-trans isomer, a conformer, a meso compound, and an enantiomer or a diastereomer.

In another preferred embodiment, the compound is selected from the group consisting of:

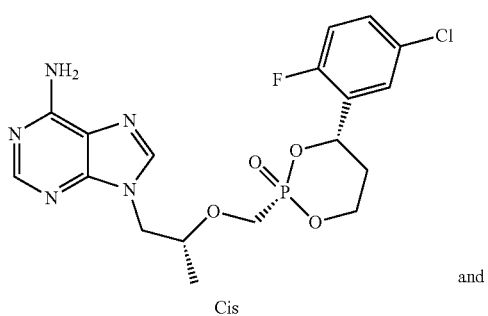

Cis and

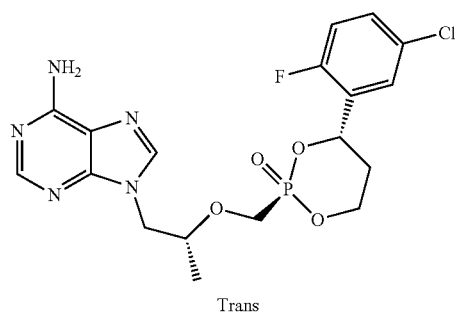

Trans

Method for Preparing Compound (Taking a Compound of Formula (III) as Example)

A monophosphate derivative Va, a 1,3-propanediol derivative Vd and dicyclohexylcarbodiimide are added into a solution prepared by N,N-dimethylformamide and pyridine in a ratio of 5:1 to produce a mixture. The mixture is heated to about 80° C. for reaction for 16 hours. After the reaction is completed, the solvent in the reaction mixture is removed using vacuum evaporation to produce a crude product. The crude product is dissolved in ethyl acetate, followed by washing with saturated NaCl solution and drying with anhydrous sodium sulfate. The resulting product was evaporated under reduced pressure to remove solvent and then was subjected to silica gel column chromatography to produce a compound of formula (II).

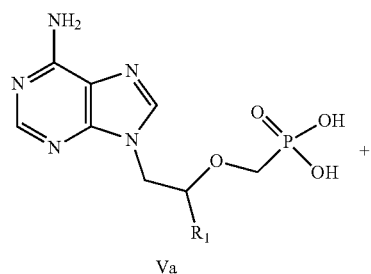

Va

+

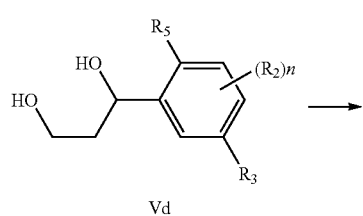

Vd

→

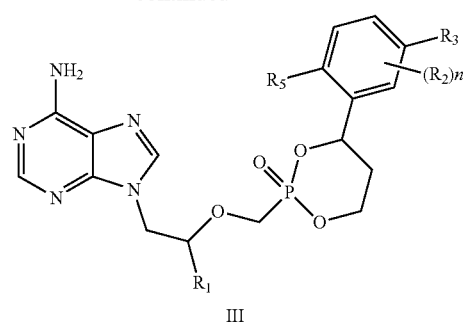

III

Wherein, each of the reactants may be commercially available or may be prepared with commercially available raw materials using a conventional method in the art.

In a preferred embodiment of the present invention, the 1,3-propanediol derivative Vd (preferably a chiral 1,3-propanediol derivative) is prepared using the following method:

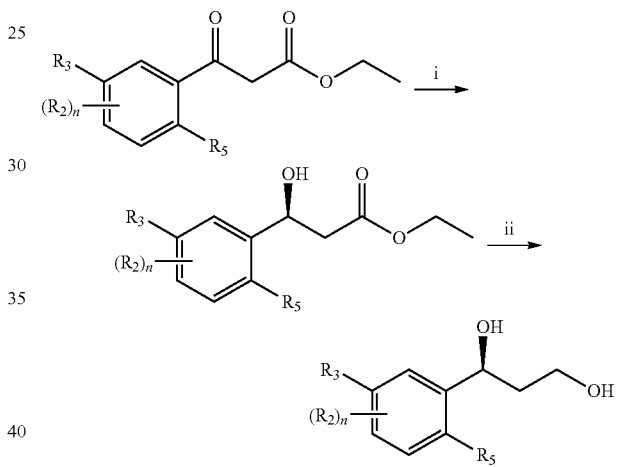

(i) reducing

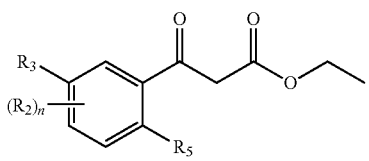

at 40-80° C. (for example, for 1-5 hours) in the presence of HCOOH, Et$_3$N and (R,R)—N-(p-Toluenesulfonyl)-1,2-diphenylethanediamine(chloro)(p-cymene)ruthenim(II) in an inert solvent (for example, DMF) to produce

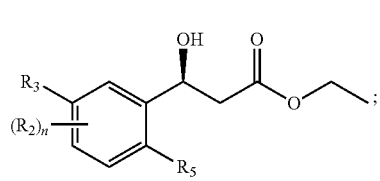

and (ii) reacting a reductant (such as NaBH₄) with

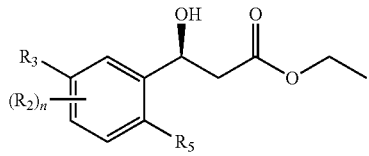

(for example, for 1-5 hours) in an amphoteric solvent (for example, EtOH) to produce

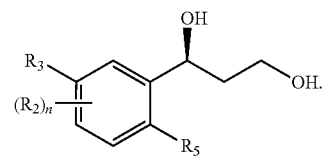

In another preferred embodiment,

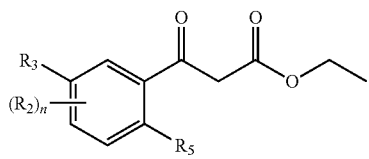

is prepared using any one of the following methods 1-3.
Method 1

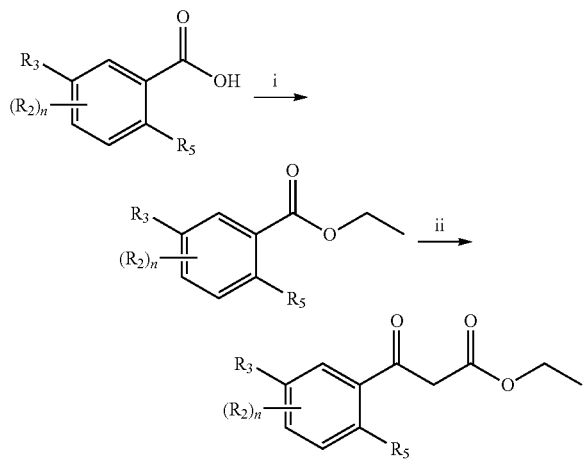

(i) reacting SOCl₂ with

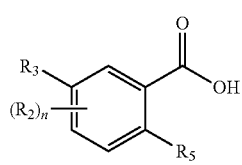

in an amphoteric solvent (for example, EtOH) to produce

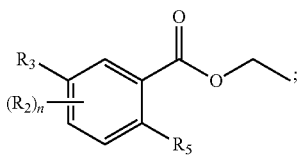

and (ii) reacting ethyl acetate with

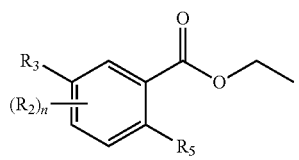

at −60 to −20° C. (for example, for 10-30 minutes) in the presence of a base (for example, LiHMDS) in an inert solvent to (for example, THF) produce

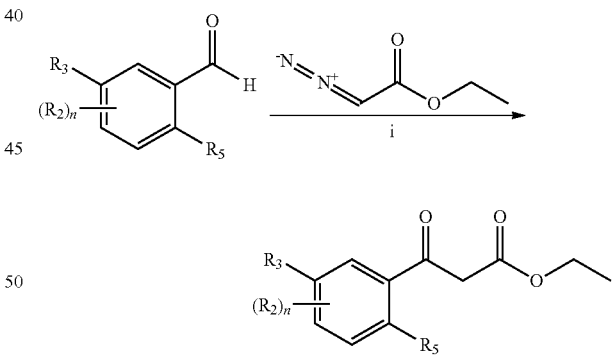

Method 2

(i) reacting at room temperature in the presence of SnCl₂ in an inert solvent (such as DCM) to produce

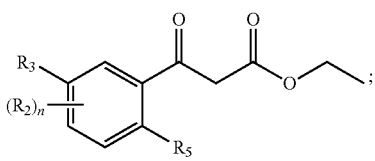

Method 3

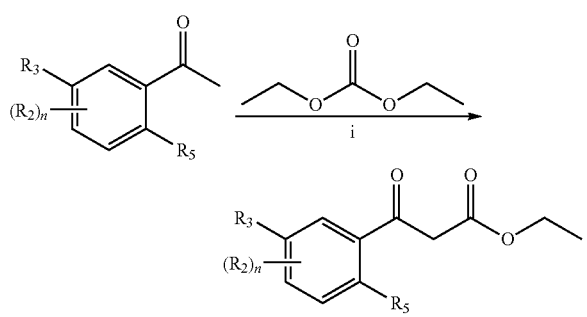

(i) reacting

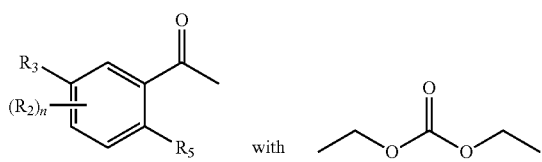

at a reflux temperature overnight in the presence of a base (for example, potassium tert-butoxide) in an inert solvent (for example, THF) to produce

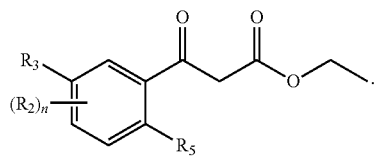

It should be understood that the above methods merely take the compound of formula (III) as an example, and those skilled in the art may reach other compounds of formula (I) or (II) through simple replacement of the corresponding raw materials.

Pharmaceutical Composition and Administration

Due to their excellent inhibitory activity against hepatitis B virus (HBV), the compound of the present invention and various crystal forms thereof, pharmaceutically acceptable inorganic or organic salts, hydrates or solvates thereof and a pharmaceutical composition comprising the compound of the present invention as a main active ingredient can be used to cure, prevent and alleviate the diseases caused by hepatitis B virus. According to the prior art, the compound of the present invention can be used for the treatment of diseases including the diseases caused by HBV, HDV or HIV infection.

The pharmaceutical composition of the present invention includes the compound of the present invention or a pharmaceutically acceptable salt thereof at a safe and effective amount, and a pharmaceutically acceptable excipient or carrier. Where, the "safe and effective amount" refers to an amount at which the compound used is sufficient to significantly improve symptoms without causing serious side effects. In general, the pharmaceutical composition includes the compound of the present invention at 0.1-1000 mg per dose, and preferably 0.5-500 mg per dose. Preferably, the "per dose" refers to a capsule or tablet.

"Pharmaceutically acceptable carrier" refers to one or more compatible solid or liquid fillers or gel materials which are suitable for human use and must be of sufficient purity and sufficiently low toxicity. The "compatibility" indicates herein that each component of a composition is capable of blending with each other and with the compound of the invention without significantly reducing the effect of the compound. Parts of the pharmaceutically acceptable carriers include cellulose and its derivatives (such as sodium carboxymethylcellulose, sodium ethylcellulose and cellulose acetate), gelatin, talc, solid lubricants (such as stearic acid and magnesium stearate), calcium sulfate, vegetable oils (such as soybean oil, sesame oil, peanut oil and olive oil), polyols (such as propylene glycol, glycerin, mannitol and sorbitol), emulsifiers (such as Tween®), wetting agents (such as sodium dodecyl sulfate), colorants, flavoring agents, stabilizers, antioxidants, preservatives and pyrogen-free water.

The administrations of the compound or pharmaceutical composition of the present invention are not particularly limited, and representative administrations include but are not limited to: oral, rectal, parenteral (intravenous, intramuscular or subcutaneous) and topical administrations, and particularly preferably oral administration.

Solid preparations for oral administration include capsules, tablets, pills, powders and granules. In such solid preparations, the active compound is mixed with at least one conventional inert excipient (or carrier) such as sodium citrate or dicalcium phosphate, or mixed with the following components including: (a) a filler or compatibilizer such as starch, lactose sucrose, glucose, mannitol and silicic acid; (b) a binder such as hydroxymethylcellulose, alginates, gelatin, polyvinylpyrrolidone, sucrose and gum arabic; (c) a humectant such as glycerol; (d) a disintegrating agent, such as agar, calcium carbonate, potato starch or tapioca starch, alginic acid, some composite silicates and sodium carbonate; (e) a retarding solvent, such as paraffin; (0 an absorbing accelerator, such as a quaternary amine compound; (g) a wetting agent, such as cetanol and glyceryl monostearate; (h) an adsorbent, such as kaoline; and (i) a lubricant, such as talc, calcium stearate, magnesium stearate, solid polyethylene glycol, sodium dodecyl sulfate, or a mixture thereof. A buffer may also be included in capsule, tablet and pill preparations.

Solid preparations, such as tablet, sugar pill, capsule, pill and granule can be prepared using a coating or shell, such as enteric coating and other materials known in the art. Such preparations may include an opacifying agent, and the release of the active compound or the compound of the composition may be carried out in a certain part of digestive tract in a tardive manner. Embedding components such as polymeric materials and waxy materials may be employed herein. If necessary, the active compound may also be used to prepare a microencapsule with one or more of the above excipients.

Liquid preparations used for oral administration include pharmaceutically acceptable emulsion, solution, suspension, syrup or tincture. In addition to the active compound, the liquid preparations may also include an inert diluent conventionally used in the art, such as water or other solvents, solubilizer and emulsifier, including ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or a mixture thereof.

In addition to such inert diluents, the composition may also comprise an auxiliary, such as wetting agent, emulsifier, suspending agent, sweetener, corrigent and spice.

In addition to the active compound, the suspension may comprise a suspending agent such as ethoxylated isostearyl alcohol, polyoxyethylene sorbitol, a sorbitan ester, microcrystalline cellulose, aluminum methoxide and agar, or a mixture thereof.

The composition for parenteral injection may comprise a physiologically acceptable sterile aqueous or anhydrous solution, a dispersion, a suspension or an emulsion, and sterile powder for reconstitution into a sterile injectable solution or dispersion. Appropriate aqueous and anhydrous carriers, diluents, solvents or excipients include water, ethanol, polyols and an appropriate mixture thereof.

Preparations of the compound of the present invention for topical administration include ointments, powders, patches, sprays and inhalants. The active ingredient is mixed under sterile conditions with a physiologically acceptable carrier and any preservatives, buffering agents, or propellants which may be required if necessary.

The compounds of the present invention may be administered alone or in combination with other pharmaceutically acceptable compounds.

When using a pharmaceutical composition, a safe and effective amount of the compound of the invention is administered to a mammal (e.g., human) who needs treatment, where a pharmaceutically effective dosage is employed for administration. For a human weighing 60 kg, the daily dose is 0.2-1000 mg, preferably 0.5-500 mg. Of course, other factors including administration routes and health condition of the patient should be taken into consideration for the specific dose, which is within the skill of the skilled physician.

Advantages of the present invention are described as follows:

(1) highly effective liver-specific delivery: the compound can only be catalyzed specifically in hepatocytes with CYP3A of the cytochrome P450 isozyme family to produce an active molecule, which has a high electronegativity and is not easy to be discharged from the liver, leading to a higher concentration in the liver, thus achieving the specific delivery;

(2) high activity: more drugs are present in the liver due to the liver-specific delivery, and the antiviral activity are also greatly improved.

(3) low toxic and side effect: when the same amount of prodrugs is used, the amount of active molecules formed outside the liver by metabolism is very small, leading to a greatly reduced kidney and bone toxicity.

The invention will be further illustrated below in conjunction with specific embodiments. It should be understood that these embodiments are merely used to illustrate the invention but not intended to limit the scope of the invention. In the following examples, the experimental methods of which the specific conditions are not specified, are usually carried out according to conventional conditions or the conditions recommended by the manufacturer. Unless otherwise specified, percentage and portion are calculated by weight herein.

Example 1

Preparation of (2R)-9-{2-[(4S)-4-(3-chloro-2-fluorophenyl)-2-oxo-1,3,2-dioxaphosphorinan-2-yl]methoxypropyl}adenine 84 mg (0.294 mmol) of (R)-9-[2-(phosphonomethoxy)propyl]adenine was dissolved in a solution prepared by 15 mL of N,N-dimethylformamide and 3 mL of pyridine to which 182 mg (0.882 mmol) of dicyclohexylcarbodiimide and 60 mg (0.294 mmol) of (S)-3-(3-chloro-2-fluorophenyl)-1,3-propanediol were added. The mixture was heated to 80° C. to react for 16 hours. After the reaction was completed, the reaction mixture was evaporated under vacuum to remove the solvent so as to produce a crude product. The crude product was dissolved in ethyl acetate followed by washing with saturated NaCl solution and drying with anhydrous sodium sulfate. The resulting product was evaporated under reduced pressure to remove solvent and then was subjected to silica gel column chromatography (a ratio of dichloromethane to methanol ranges from 20:1 to 10:1) to produce a white solid product with a yield of 41% and $R_f$ of 0.4 (a ratio of dichloromethane to methanol is 10:1).

$^1$H NMR (400 MHz, DMSO-d$_6$) δ: 8.071-8.227 (m, 2H), 7.202-7.661 (m, 5H), 5.837-5.961 (m, 1H), 4.549-4.603 (m, 1H), 3.935-4.356 (m, 6H), 1.914-2.119 (m, 2H), 1.105-1.198 (m, 3H) ppm.

Example 2

Preparation of (2R)-9-{2-[(4S)-4-(3-chloro-5-fluorophenyl)-2-oxo-1,3,2-dioxaphosphorinan-2-yl]methoxypropyl}adenine This embodiment employed a method similar to that of Example 1. 84 mg (0.294 mmol) of (R)-9-[2-(phosphonomethoxy) propyl]adenine, 182 mg (0.882 mmol) of dicyclohexylcarbodiimide and 60 mg (0.294 mmol) of (S)-3-(3-chloro-5-fluorophenyl)-1,3-propanediol were reacted to produce 35 mg of a white solid product with a yield of 26% and $R_f$ of 0.4 (a ratio of dichloromethane to methanol is 10:1).

$^1$H NMR (400 MHz, DMSO-d$_6$): δ: 8.045-8.163 (m, 2H), 7.173-7.455 (m, 5H), 5.621-5.681 (m, 1H), 4.228-4.271 (m, 1H), 4.001-4.059 (m, 6H), 1.952-2.109 (m, 2H), 1.097-1.196 (m, 3H) ppm.

Example 3

Preparation of (2R)-9-{2-[(4S)-4-(3-chloro-4-fluorophenyl)-2-oxo-1,3,2-dioxaphosphorinan-2-yl]methoxypropyl}adenine This embodiment employed a method similar to that of Example 1. 118 mg (0.412 mmol) of (R)-9-[2-(phosphonomethoxy) propyl]adenine, 254.6 mg (1.236 mmol) of dicyclohexylcarbodiimide and 84 mg (0.412 mmol) of (S)-3-(3-chloro-4-fluorophenyl)-1,3-propanediol were reacted completely to produce 71 mg of a white solid product with a yield of 37.8% and $R_f$ of 0.4 (a ratio of dichloromethane to methanol is 10:1).

$^1$H NMR (400 MHz, DMSO-d$_6$): δ: 8.056-8.151 (m, 2H), 7.552-7.584 (m, 1H), 7.205-7.493 (m, 4H), 5.556-5.618 (m, 1H), 4.427-4.502 (m, 1H), 3.922-4.303 (m, 6H), 1.813-2.016 (m, 2H), 1.095-1.193 (m, 3H) ppm.

Example 4

Preparation of (2R)-9-{2-[(4S)-4-(5-chloro-2-fluorophenyl)-2-oxo-1,3,2-dioxaphosphorinan-2-yl]methoxypropyl}adenine This embodiment employed a method similar to that of Example 1. 112 mg (0.39 mmol) of (R)-9-[2-(phosphonomethoxy) propyl]adenine, 242 mg (1.176 mmol) of dicyclohexylcarbodiimide and 80 mg (0.39 mmol) of (S)-3-(5-chloro-2-fluorophenyl)-1,3-propanediol were reacted completely to produce 60 mg of a white solid product with a yield of 38% and $R_f$ of 0.3 (a ratio of dichloromethane to methanol is 10:1).

$^1$H NMR (400 MHz, DMSO-d$_6$): δ: 8.048-8.225 (m, 2H), 7.182-7.545 (m, 5H), 5.825-5.911 (m, 1H), 4.536-4.593 (m, 1H), 3.971-4.339 (m, 6H), 1.893-2.172 (m, 2H), 1.103-1.196 (m, 3H) ppm.

15.66 g of (2R)-9-{2-[(4S)-4-(5-chloro-2-fluorophenyl)-2-oxo-1,3,2-dioxaphosphorinan-2-yl]methoxypropyl}adenine was passed through a chiral column to produce 9.69 g of (2R)-9-{2-[(2R, 4S)-4-(5-chloro-2-fluorophenyl)-2-oxo-1,3,2-dioxaphosphorinan-2-yl]methoxypropyl}adenine under the following conditions:
column: CHIRALPAK ADH;
mobile phase: ethanol and acetonitrile mixed in a volume ratio of 90:10;
wavelength: 254 nm; and
temperature: 25° C.

$^1$H NMR (400 MHz, Methanol-D4): δ: 8.19 (s, 1H), 8.14 (s, 1H), 7.43-7.34 (m, 2H), 7.19-7.11 (m, 1H), 5.86 (t, J=7.0 Hz, 1H), 4.70-4.60 (m, 1H), 4.46-4.26 (m, 3H), 4.16-4.08 (m, 1H), 4.05 (t, J=7.3 Hz, 2H), 2.16-2.08 (m, 2H), 1.30 (d, J=6.2 Hz, 3H) ppm.

Example 5

Preparation of (2R)-9-{2-[(4S)-4-(4-pyridine)-2-oxo-1,3,2-dioxaphosphorinan-2-yl]methoxypropyl}adenine This embodiment employed a method similar to that of Example 1. 112 mg (0.39 mmol) of (R)-9-[2-(phosphonomethoxy) propyl]adenine, 242 mg (1.176 mmol) of dicyclohexylcarbodiimide and 80 mg (0.39 mmol) of (S)-3-(4-pyridine)-1,3-propanediol were reacted completely to produce 70 mg of a white solid product with a yield of 39% and $R_f$ of 0.4 (a ratio of dichloromethane to triethylamine to methanol is 10:1:0.1).

$^1$H NMR (400 MHz, DMSO-d$_6$): δ: 8.595-8.629 (m, 1H), 8.545 (d, J=4.8 HZ, 1H), 8.070-8.169 (m, 2H), 7.213-7.350 (m, 4H), 5.591-5.662 (m, 1H), 4.483-4.559 (m, 1H), 3.913-4.345 (m, 6H), 1.913-2.114 (m, 2H), 1.100-1.178 (m, 3H) ppm.

Example 6

Preparation of (2R)-9-{2-[(2R, 4S)-4-(3-chloro-5-fluorophenyl)-2-oxo-1,3,2-dioxaphosphorinan-2-yl]methoxypropyl}adenine and (2R)-9-{2-[(2S, 4S)-4-(3-chloro-5-fluorophenyl)-2-oxo-1,3,2-dioxaphosphorinan-2-yl]methoxypropyl}adenine 410.7 mg of (2R)-9-{2-[(4S)-4-(3-chloro-5-fluorophenyl)-2-oxo-1,3,2-dioxaphosphorinan-2-yl]methoxypropyl}adenine was passed through a chiral column under the following conditions to produce diastereomers thereof: 220.2 mg of (2R)-9-{2-[(2R, 4S)-4-(3-chloro-5-fluorophenyl)-2-oxo-1,3,2-dioxaphosphorinan-2-yl]methoxypropyl}adenine and 166.2 mg of (2R)-9-{2-[(2S, 4S)-4-(3-chloro-5-fluorophenyl)-2-oxo-1,3,2-dioxaphosphorinan-2-yl]methoxypropyl}adenine.

(2R)-9-{2-[(2R, 4S)-4-(3-chloro-5-fluorophenyl)-2-oxo-1,3,2-dioxaphosphorinan-2-yl]methoxypropyl}adenine: $^1$H NMR (400 MHz, CDCl$_3$): δ:8.350 (S, 1H), 7.930 (S, 1H), 7.074-7.100 (m, 2H), 6.890 (d, J=8.8 Hz, 1H), 5.735 (s, 2H), 5.585 (d, J=10.4 Hz, 1H), 4.655-4.711 (m, 1H), 4.343-4.429 (m, 2H), 4.157-4.212 (m, 1H), 3.970-4.059 (m, 2H), 3.801-3.860 (m, 1H), 2.014-2.108 (m, 2H), 1.316 (d, J=6.4 Hz, 3H) ppm.

(2R)-9-{2-[(2S, 4S)-4-(3-chloro-5-fluorophenyl)-2-oxo-1,3,2-dioxaphosphorinan-2-yl]methoxypropyl}adenine: $^1$H NMR (400 MHz, CDCl$_3$): δ:8.372 (m, 1H), 7.905 (s, 1H), 7.011-7.157 (m, 3H), 5.899 (s, 2H), 5.432 (d, J=11.2 Hz, 1H), 3.897-4.410 (m, 7H), 2.141-2.249 (m, 1H), 1.763-1.800 (m, 1H), 1.337 (d, J=6.4 Hz, 3H) ppm.

Column: CHIRALPAK ADH.
Mobile phase: ethanol and acetonitrile mixed in a volume ratio of 90:10.
Wavelength: 254 nm.
Temperature: 25° C.

Comparative Example 7 Preparation of (2R)-9-{2-[(4S)-4-(3-chlorophenyl)-2-oxo-1,3,2-dioxaphosphorinan-2-yl]methoxy propyl}adenine This embodiment employed a method similar to that of Example 1. 660 mg (2.419 mmol) of (R)-9-[2-(phosphonomethoxy)propyl]adenine, 1.5 g (7.257 mmol) of dicyclohexylcarbodiimide and 450 mg (2.419 mmol) of (S)-3-(3-chlorophenyl)-1,3-propanediol were reacted completely to produce 400 mg of a white solid product with a yield of 38% and $R_f$ of 0.5 (a ratio of dichloromethane to methanol is 10:1).

$^1$H NMR (400 MHz, DMSO-d$_6$): δ: 7.872-8.296 (m, 2H), 7.211-7.269 (m, 4H), 6.019-6.077 (m, 2H), 5.523-5.550 (m, 1H), 4.261-4.357 (m, 1H), 3.773-4.156 (m, 6H), 1.907-1.990 (m, 2H), 1.236-1.354 (m, 3H) ppm.

Comparative Example 8 Preparation of (2R)-9-{2-[(4S)-4-(3,5-dichlorophenyl)-2-oxo-1,3,2-dioxaphosphorinan-2-yl]meth oxypropyl}adenine This embodiment employed a method similar to that of Example 1. 84 mg (0.294 mmol) of (R)-9-[2-(phosphonomethoxy) propyl]adenine, 182 mg (0.882 mmol) of dicyclohexylcarbodiimide and 60 mg (0.294 mmol) of (S)-3-(3,5-dichlorophenyl)-1,3-propanediol were reacted completely to produce 62 mg of a white solid product with a yield of 45% and $R_f$ of 0.4 (a ratio of dichloromethane to methanol is 10:1).

$^1$H NMR (400 MHz, CDCl$_3$): δ:8.346-8.378 (m, 1H), 7.909-7.939 (m, 1H), 7.351-7.363 (m, 1H), 7.265-7.268 (m, 1H), 7.178-7.181 (m, 1H), 5.770-5.825 (m, 2H), 5.399-5.588 (m, 1H), 3.808-4.428 (m, 7H), 2.025-2.085 (m, 2H), 1.306-1.349 (m, 3H) ppm.

Comparative Example 9

Preparation of (2R)-9-{2-[(2R, 4S)-4-(3-chlorophenyl)-2-oxo-1,3,2-dioxaphosphorinan-2-yl]methoxypropyl}adenine (2R)-9-{2-[(2R, 4S)-4-(3-chlorophenyl)-2-oxo-1,3,2-dioxaphosphorinan-2-yl]methoxypropyl}adenine was prepared using the technical solution disclosed in J. Am. Chem. Soc. 2004, 126, 5154-5163.

$^1$H NMR (400 MHz, CDCl$_3$): δ:8.352 (s, 1H), 7.907 (s, 1H), 7.285-7.354 (m, 3H), 7.106 (d, J=6.8 Hz, 1H), 5.802 (s, 2H), 5.591 (d, J=10.8 Hz, 1H), 4.624-4.681 (m, 1H), 4.443-4.468 (m, 2H), 4.235-4.321 (m, 1H), 3.899-4.031 (m, 4H), 1.980-2.109 (m, 2H) ppm.

TABLE 1

Compounds prepared in various Examples

| Compound number | Structure | Name | MS |
|---|---|---|---|
| 1 (PA1008-racemate) | 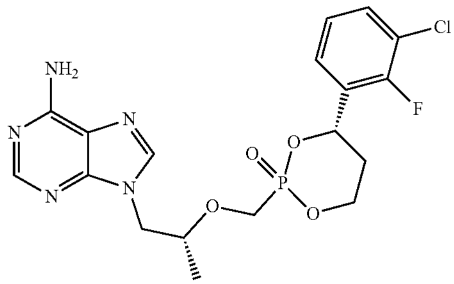 [SMILES: C[C@H](Cn1cnc2c(N)ncnc21)OCP1(=O)OCC[C@@H](c2cccc(Cl)c2F)O1] | (2R)-9-{2-[(4S)-4-(3-chloro-2-fluorophenyl)-2-oxo-1,3,2-dioxaphosphorinan-2-yl]methoxypropyl}adenine | 455.81 |
| 2 (PA1007-racemate) | 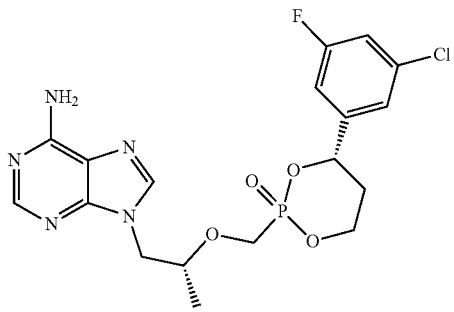 [SMILES: C[C@H](Cn1cnc2c(N)ncnc21)OCP1(=O)OCC[C@@H](c2cc(F)cc(Cl)c2)O1] | (2R)-9-{2-[(4S)-4-(3-chloro-5-fluorophenyl)-2-oxo-1,3,2-dioxaphosphorinan-2-yl]methoxypropyl}adenine | 455.81 |
| 3 (PA1009-racemate) | 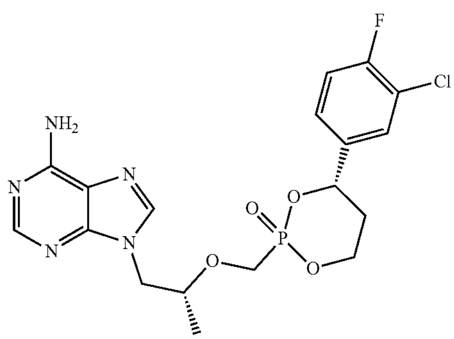 [SMILES: C[C@H](Cn1cnc2c(N)ncnc21)OCP1(=O)OCC[C@@H](c2ccc(F)c(Cl)c2)O1] | (2R)-9-{2-[(4S)-4-(3-chloro-4-fluorophenyl)-2-oxo-1,3,2-dioxaphosphorinan-2-yl]methoxypropyl}adenine | 455.81 |
| 4 (PA1010-racemate) | 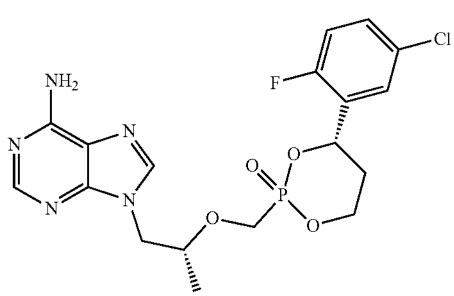 [SMILES: C[C@H](Cn1cnc2c(N)ncnc21)OCP1(=O)OCC[C@@H](c2cc(Cl)ccc2F)O1] | (2R)-9-{2-[(4S)-4-(5-chloro-2-fluorophenyl)-2-oxo-1,3,2-dioxaphosphorinan-2-yl]methoxypropyl}adenine | 455.81 |
| 4-cis (PA1010-cis) | 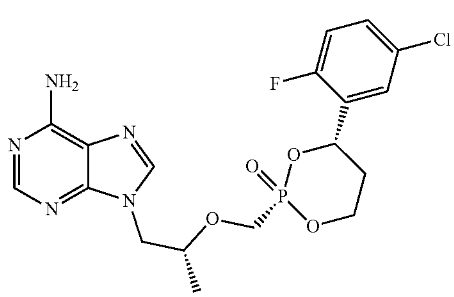 [SMILES: C[C@H](Cn1cnc2c(N)ncnc21)OC[P@@]1(=O)OCC[C@@H](c2cc(Cl)ccc2F)O1] | (2R)-9-{2-[(2R,4S)-4-(5-chloro-2-fluorophenyl)-2-oxo-1,3,2-dioxaphosphorinan-2-yl]methoxypropyl}adenine | 455.81 |

TABLE 1-continued

Compounds prepared in various Examples

| Compound number | Structure | Name | MS |
|---|---|---|---|
| 4-trans (PA1010-trans) | 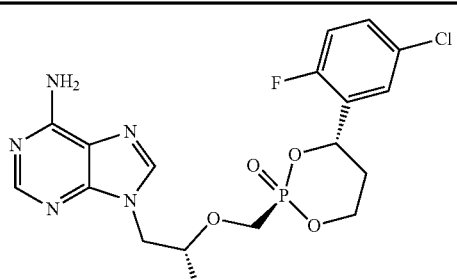 | (2R)-9-{2-[(2S, 4S)-4-(5-chloro-2-fluorophenyl)-2-oxo-1,3,2-dioxaphosphorinan-2-yl]methoxypropyl}adenine | 455.81 |
| 5 (PA1006-racemate) | 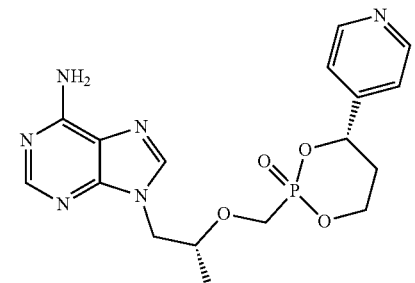 | (2R)-9-{2-[(4S)-4-(4-pyridine)-2-oxo-1,3,2-dioxaphosphorinan-2-yl]methoxypropyl}adenine | 404.36 |
| 6-cis (PA1007-cis) | 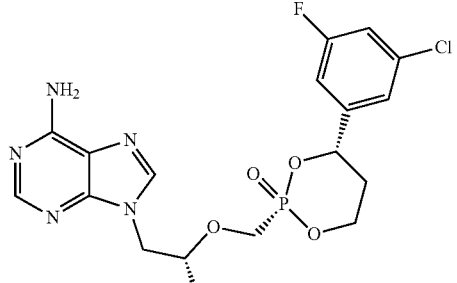 | (2R)-9-{2-[(2R, 4S)-4-(3-chloro-5-fluorophenyl)-2-oxo-1,3,2-dioxaphosphorinan-2-yl]methoxypropyl}adenine | 455.81 |
| 6-trans (PA1007-trans) | 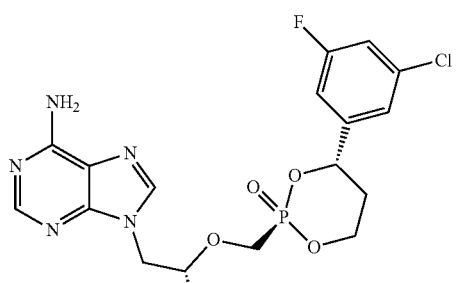 | (2R)-9-{2-[(2S, 4S)-4-(3-chloro-5-fluorophenyl)-2-oxo-1,3,2-dioxaphosphorinan-2-yl]methoxypropyl}adenine | 455.81 |
| Comparative example 7 (PA1002-racemate) | 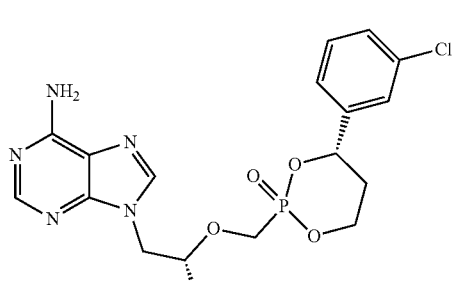 | (2R)-9-{2-[(4S)-4-(3-chlorophenyl)-2-oxo-1,3,2-dioxaphosphorinan-2-yl]methoxypropyl}adenine | 437.82 |

TABLE 1-continued

Compounds prepared in various Examples

| Compound number | Structure | Name | MS |
|---|---|---|---|
| Comparative example 8 (PA1005-racemate) | 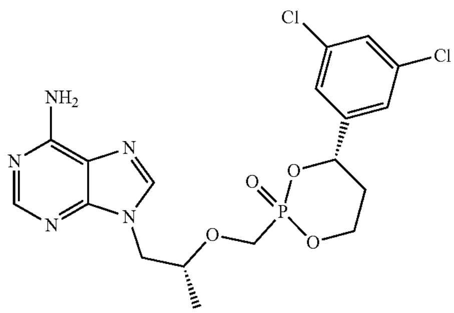 [SMILES: C[C@H](Cn1cnc2c(N)ncnc21)OCP1(=O)OCC[C@@H](c2cc(Cl)cc(Cl)c2)O1] | (2R)-9-{2-[(4S)-4-(3,5-dichlorophenyl)-2-oxo-1,3,2-dioxaphosphorinan-2-yl]methoxypropyl}adenine | 472.26 |
| Comparative example 9 (Pradefovir) | 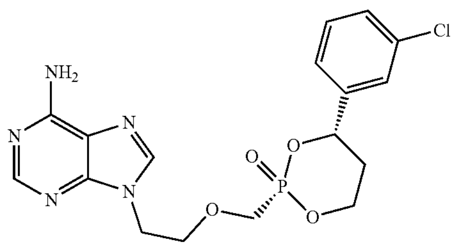 [SMILES: Nc1ncnc2c1ncn2CCOC[P@@]1(=O)OCC[C@@H](c2cccc(Cl)c2)O1] | (2R)-9-{2-[(2R,4S)-4-(3-chlorophenyl)-2-oxo-1,3,2-dioxaphosphorinan-2-yl]methoxypropyl}adenine | 423.79 |

Notes:
unless otherwise specified, PA1010 used herein is PA1010-cis, and PA1007 used herein is PA1007-cis.

Example 11

Evaluation of Active Molecules Formed by Metabolism In Vitro with CYP3A4 Enzyme Measuring Method The evaluation was performed by determining the metabolism efficiency of from 0.1 µM of prodrugs to active molecules (PMPA or PMEA) in the presence of 1 mg/mL of a recombinant human CYP3A4 enzyme (CYPEX). The enzymatic reaction was carried out in 500 µL of a 0.1 M Tris-HCl buffer solution (pH 7.4), and the reaction system further contained 5 mM of magnesium chloride and 1 mM of NADPH. The reaction mixture was incubated in a constant temperature shaking water bath at 37° C. and sampled after 0, 7, 17, 30 minutes, respectively, and the reaction was terminated by adding methanol 1.5 times the volume of the reaction mixture. The samples were centrifuged at a maximum speed of 13,600 rpm for 20 minutes using an Eppendorf tabletop centrifuge. The supernatant was collected and dried with a nitrogen evaporator, and then redissolved with mobile phase A (an aqueous solution containing 5 mM of ammonium acetate and 0.05% by volume formic acid). The resulting solution was analyzed using LS-MS/MS (Waters, Acquity UPLC HSS T3 column).

TABLE 2

Amount of active molecules derived from in-vitro metabolism with CYP3A4 enzyme

| Compound number | Configuration | Active molecule production/initial concentration (%) (30 min) |
|---|---|---|
| 1 | S-configuration racemate | 4.00 |
| 2 | S-configuration racemate | 13.29 |
| 3 | S-configuration racemate | 3.57 |
| 4 | S-configuration racemate | 5.58 |
| 5 | S-configuration racemate | 2.72 |
| 6-cis | S-configuration cis | 27.36 |
| 7 | S-configuration racemate | 8.67 |
| 8 | S-configuration racemate | 1.01 |
| 9 | S-configuration cis | 17.37 |

Figure 2:
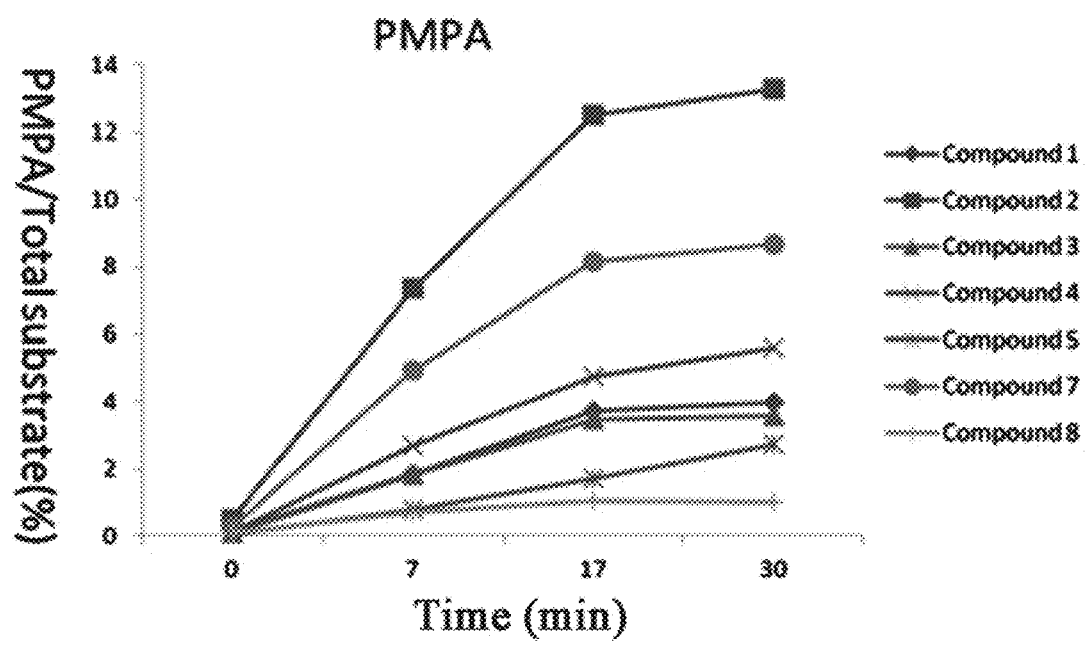
FIG. 2 shows the ratio of respective liver-specific delivery-based compounds (racemate) metabolized to active molecules in the presence of CYP3A4 enzyme. Compound names are shown in Table 1, and the active metabolic molecules corresponding to all compounds are PMPA.
Figure 3:
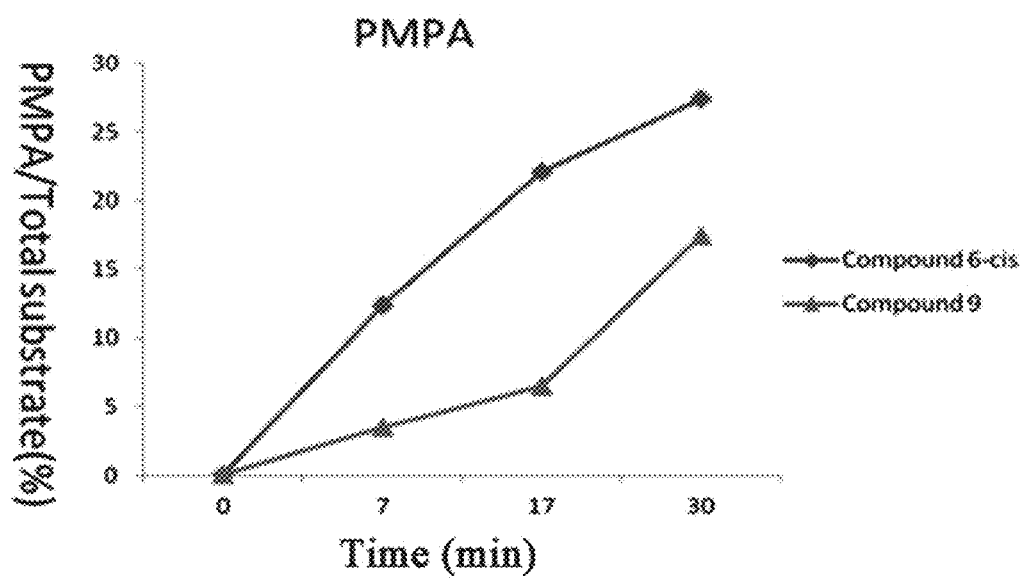
FIG. 3 shows the ratio of liver-specific delivery-based compounds (S-configuration and cis) metabolized to active molecules in the presence of CYP3A4 enzyme. Compound names are shown in Table 1 in which the active metabolic molecule corresponding to cis-compound 6 is PMPA, and the active metabolic molecule corresponding to compound 9 (Pradefovir) is PMEA.

Analysis of Results:

Compounds 1, 2, 3, 4, 5, 7 and 8 each have an S-configuration racemate structure, and compounds 6 and 9 each have an S-configuration cis structure. The results of the enzymatic metabolism for 30 minutes were shown in Table 2, and the dynamic results of the enzymatic metabolism were shown in FIGS. 2 and 3. As shown in Table 2, in the S-configuration racemate structures, the ratio of compound 2 metabolized to active metabolites PMPA was the highest (13.29%), and those of compounds 7 and 8 in Comparative examples 7 and 8 were 8.67% and 1.01%, respectively.

Compound 2 was resolved to produce an S-configuration cis compound (compound 6-cis) with a metabolism ratio of 27.36%, which had a higher metabolism ratio than that of its corresponding S-configuration racemate (compound 2).

It can be seen from the above results that the metabolism ratio of compound 2 of the present invention was about 50%-1300% higher than that of compounds of other structures. The activity of compound 2 (with different halogens of Cl and F at the 3 and 5 positions) of the present invention was about 13 times higher than that of compound 8 of which the 3 and 5 positions both were Cl.

Compound 2 with the best activity was resolved to produce a cis product compound 6-cis, and compared to the compound Pradefovir of the same type (compound 9, S-configuration cis) which has currently been used for clinical research, the activity of compound 6-cis of the present invention was still 57.5% higher.

Example 12

Evaluation of Formation of Active Molecules from In-Vitro Metabolism with Human Liver Microsomes Measuring Method Human liver microsomes used herein were purchased from In Vitro Technologies (IVT) Inc., Batch No.: SSP X008070, a mixed liver microsome extracted from the liver tissues of 150 donors. The metabolic activity of CYP3A4 in the liver microsomes of this batch was recorded in the product description to be 1.734 nmol/mg/min (a rate of metabolizing testosterone into 6-β-testosterone). The test compounds were synthesized by Zhejiang Paloalto Pharmaceutical Technology Co., Ltd., and dissolved in methanol to produce a 25 mM stock solution. The enzymatic reaction was carried out in 100 μL of a reaction solution (100 mM Tris-HCl, 5 mM $MgCl_2$, pH 7.4) at a test compound concentration of 25 μM and a human liver microsome concentration of 2 mg/mL, and NADPH was added to start the reaction (with a final concentration of 2 mM). After the reaction was performed in a constant temperature shaking water bath for 5 minutes, acetonitrile was quickly added to terminate the reaction at 1.5 times the volume of the reaction mixture. The collected samples were centrifuged at a maximum speed of 13,600 rpm for 20 minutes using an Eppendorf table top centrifuge. The supernatant was collected and dried with a nitrogen evaporator, and then redissolved with mobile phase A, which was an aqueous solution containing 5 mM of ammonium acetate and 0.05% formic acid by volume. The resulting solution was subjected to quantitative analysis using LS-MS/MS (Waters, Acquity UPLC HSS T3 column).

TABLE 3

Metabolic rates of the test compounds into PMPA or PMEA with human liver microsomes in vitro

| Compound number | Configuration | Average rate of PMPA production in 5 minutes pmol/min/mg HLM |
|---|---|---|
| 1 | S configuration racemate | 33.8 |
| 2 | S configuration racemate | 46.8 |
| 3 | S configuration racemate | 22.2 |
| 4 | S configuration racemate | 48.8 |
| 4-cis | S configuration cis | 170 |
| 6-cis | S configuration cis | 75.8 |
| 7 | S configuration racemate | 27.5 |
| 9 | S configuration cis | 20.4 |

Notes:
HLM is the abbreviation of human liver microsomes.

Analysis of Results:

Compounds 1, 2, 3, 4 and 7 each have an S-configuration racemate structure, and compounds 4-cis, 6-cis and 9-cis each have an S-configuration cis structure. The average rates of PMPA or PMEA production within 5 minutes from human liver microsome metabolism were shown in Table 3.

It can be seen from Table 3 that in the compounds of an S-configuration racemate structure, compounds 2 and 4 were metabolized to the active molecule PMPA at the highest rates of 46.8 pmol/min/mg HLM and 48.8 pmol/min/mg HLM, respectively.

Compound 2 was resolved to produce an S-configuration cis compound (compound 6-cis), of which the metabolic rate to form PMPA was 75.8 pmol/min/mg HLM, and the rate was higher than that of its corresponding S-configuration racemate (compound 2).

Compound 4 was resolved to produce an S-configuration cis compound (compound 4-cis), of which the metabolic rate to form PMPA was 170 pmol/min/mg HLM, and the rate was higher than that of its corresponding S-configuration racemate (compound 4).

As shown in the above results, compounds 2 and 4 of the present invention showed a better conversion to the active metabolic molecule PMPA than other compounds of other structures with the catalysis of human liver microsomes. Compounds 2 and 4 were resolved to produce cis products, i.e. compound 6-cis and compound 4-cis. The S-configuration cis compounds obtained through the resolution showed a better metabolic efficiency to form the active molecule compared to the compound Pradefovir of the same type (compound 9, S-configuration cis) which has currently been used in clinical research, and the metabolic efficiency of compound 4-cis was significantly superior to that of compound 6-cis. Specifically, the metabolic rate of compound 4-cis to form PMPA was 2.2 times that of compound 6-cis and was 8.3 times that of compound 9 to form PMEA.

The above results demonstrated that compound 4 of which 5 and 2 positions of the benzene ring moiety were substituted with Cl and F, respectively, and compound 2 in which 5 and 3 positions of the benzene ring moiety were substituted with F and Cl, respectively, had a superior metabolic activity to other compounds, which indicated the compound with its benzene ring asymmetrically substituted with halogens at 3 and 5 positions or 2 and 5 positions improved the activation rate of the liver-specific delivery compounds with the action of the human liver microsomes.

Example 13

Experiment of Liver-Specific Delivery Compound

1. Method
1.1 Animal Experiment
Male SD rats weighing 180-300 g were provided by Shanghai Sippr-BK Laboratory Animals Co., Ltd. Male animals were adapted to the environment for more than 3 days and fasted for 12 hours but without water deprivation at the night before the experiment. PA1010 (compound 4-cis), PA1007 (compound 6-cis), TAF and TDF were respectively dissolved in a normal saline to prepare their corresponding solutions. Before the administration, the animal's body weight was checked whether it met the experimental requirements. 12 rats were selected for grouping, 2 rats in each group, and were intragastrically administered with a drug solution at 30 mg/kg. Rats were euthanized with carbon dioxide gas at 0.5, 1, 3, 6, 12 and 24 h, respectively. Blood samples were collected from the heart and stored in a heparin anticoagulation tube. Then the samples were centrifuged at 4° C. and 6,000 rpm for 5 minutes, and the plasma supernatant was stored in ice. The kidney and liver tissues of the rats were collected and rinsed with normal saline pre-cooled at 4° C., and then stored in ice after water was drained. After the experiment, the samples were stored at −80° C. in a refrigerator.

1.2 Determination of Monophosphate Metabolite Tenofovir (PMPA) of PA1010, PA1007, TAF and TDF in Biological Samples Sample Pretreatment The kidney and liver tissues were disrupted and mixed thoroughly in normal saline 5 times the volume of the kidney and liver tissues to obtain a tissue homogenate sample. 100 μL of the rat plasma or tissue homogenate sample was mixed uniformly with 100 μL of 10% trichloroacetic acid precipitant containing 50 ng/mL of adefovir (internal standard) and the solvent thereof was prepared by methanol and acetonitrile in a volume ratio of 50:50. The mixture was centrifuged at 4° C. and 6000 rpm for 5 minutes, and all supernatant was treated with a SPE microextraction plate (MCX μElution Plate 30 μm, Waters). Finally, the microextraction plate was eluted with a methanol solution containing 5% ammonia, and 75 μL of the obtained eluent was transferred to a 384-well sample plate for analysis with an injection volume of 1 μL.

Gas Chromatography-Mass Spectrometry Conditions

LC-MS/MS-AJ (Triple Quad 5500, AB SCIEX) was used for sample analysis. The chromatographic conditions were shown as follows: chromatographic column: Acquity UPLC HSS T3 (2.1×50 mm, 1.8 μm); column temperature: 40° C.; flow rate: 0.5 mL/min; mobile phase A: 0.1% formic acid aqueous solution and mobile phase B: an acetonitrile solution. The sample was separated using gradient elution, and the program was shown in Table 4. The mass spectrometry conditions corresponding to the internal standard were shown as follows: electrospray ionization (ESI): positive ion mode; ion pair m/z monitored by multiple reaction monitoring (MRM): 288/176 (PMPA), 274/162 (PMEA); capillary voltage: 3.0 kV; temperature: 500° C.; desolvation gas flow: 1000 L/h; scanning time: 0.025 seconds; and collision energy: 25 V.

TABLE 4

LC gradient elution conditions of PMPA

| Time (min) | Mobile phase B (%) |
|---|---|
| 0 | 1 |
| 1.1 | 10 |
| 1.5 | 80 |
| 2.5 | 1 |

1.3 Data Analysis

Bar charts of the concentration of PMPA in plasma, liver and kidney corresponding to time were respectively plotted. The area (AUC0-t) under the tissue concentration-time curve of PMPA was fitted using the log-linear trapezoidal method in a non-compartmental model of WinNonLin 6.2.1 (Pharsight, CA). The ratios of liver to kidney and liver to plasma of PMPA were obtained by calculating the ratio of their corresponding AUC0-t.

2. Results

Figure 4:
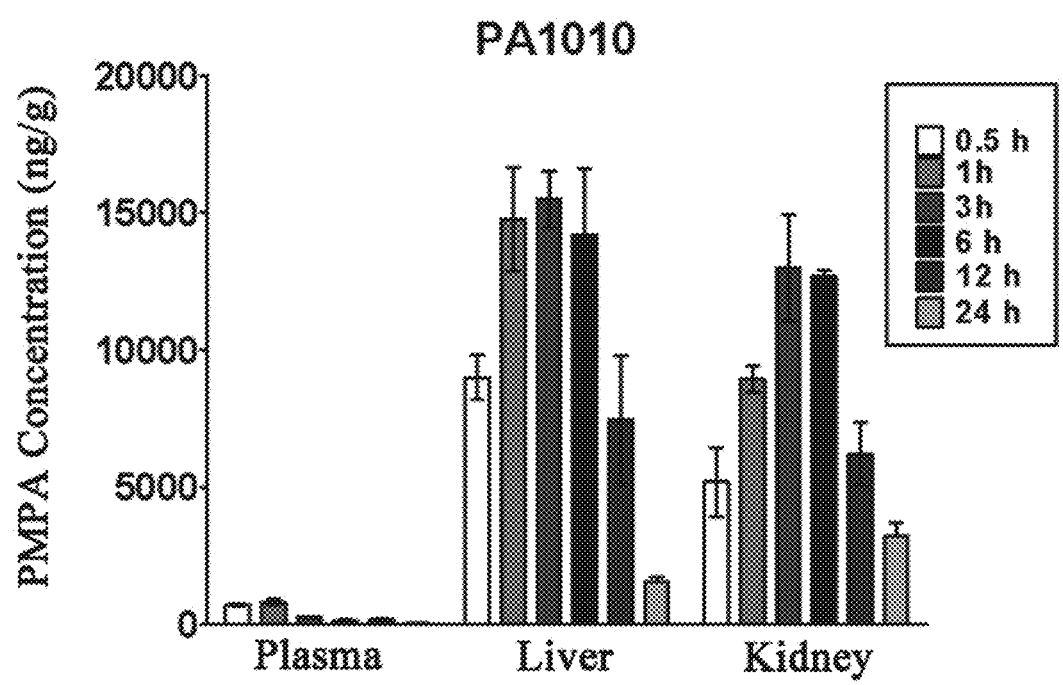
FIG. 4 is a bar chart showing concentrations of the active molecule PMPA released by in-vivo metabolism in plasma, liver and kidney over time after intragastric administration of 30 mg/kg PA1010 to rats. Compound names are shown in Table 1.
Figure 5:
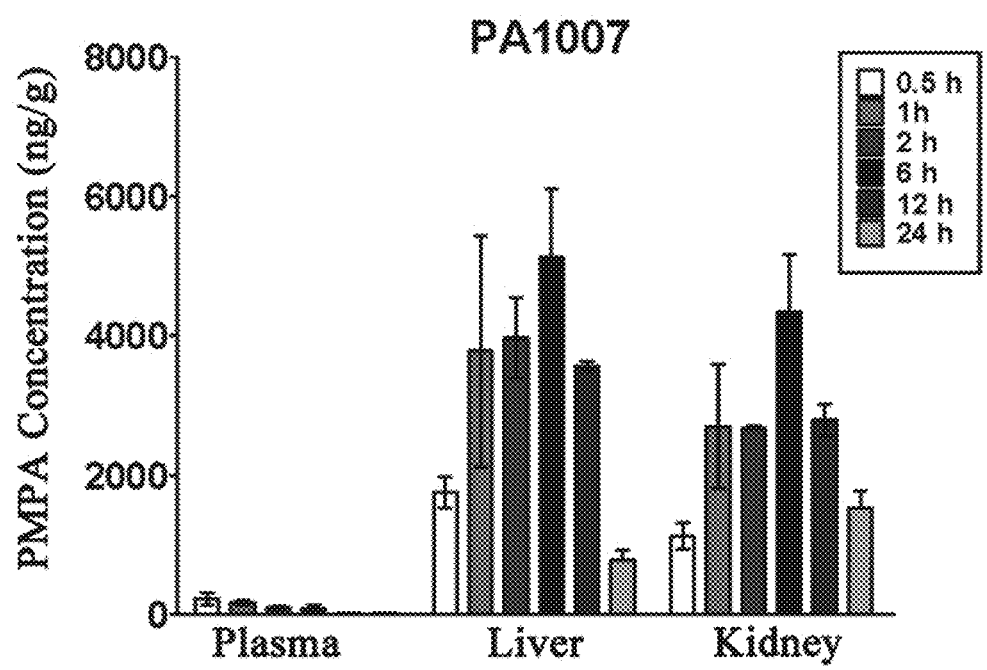
FIG. 5 is a bar chart showing concentrations of the active molecule PMPA released by in-vivo metabolism in plasma, liver and kidney over time after intragastric administration of 30 mg/kg PA1007 to rats. Compound names are shown in Table 1.
Figure 6:
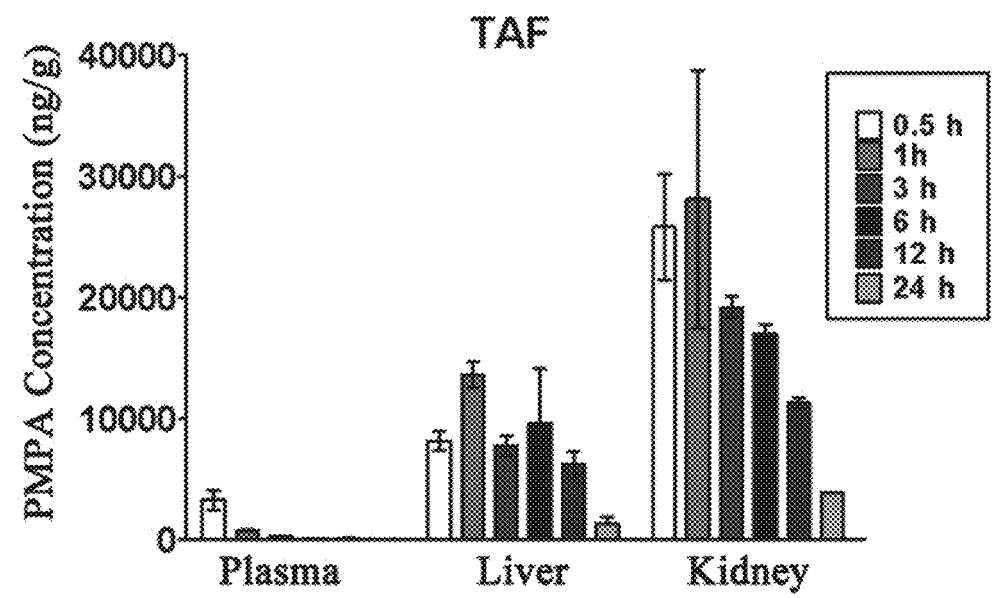
FIG. 6 is a bar chart showing concentrations of the active molecule PMPA released by in-vivo metabolism in plasma, liver and kidney over time after intragastric administration of 30 mg/kg TAF to rats.
Figure 7:
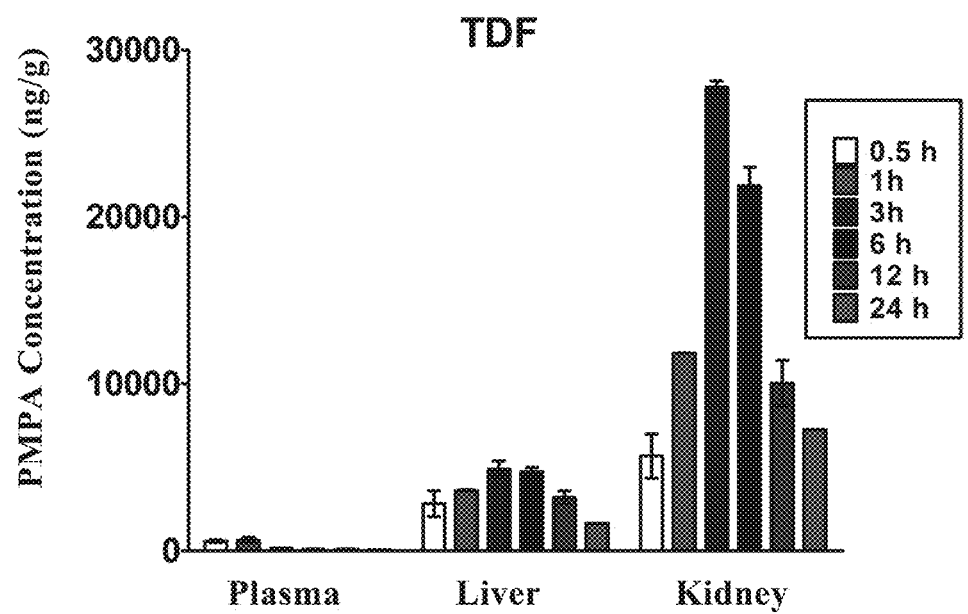
FIG. 7 is a bar chart showing concentrations of the active molecule PMPA released by in-vivo metabolism in plasma, liver and kidney over time after intragastric administration of 30 mg/kg TDF to rats.

After the rats were intragastrically administered with the drug solution of 30 mg/kg, the results of distribution in liver tissues indicated that the active molecule PMPA level released through PA1010 metabolism was significantly higher than that released through TAF and TDF metabolism at the corresponding time points ($p<0.01$, FIGS. 4, 6 and 7). The area under the drug concentration-time curve was fitted using WinNonLin 6.2.1. Referring to Table 5, the exposure levels of PMPA in liver released from each test drug were compared: PA1010>TAF>PA1007>TDF, and the exposure level of PMPA in the liver released from PA1010 was 1.5 and 2.9 times those released from TAF (222692 h·ng/g to 148407 h·ng/g) and TDF (222692 h·ng/g to 78050 h·ng/g), respectively. The results indicated that to achieve the same clinical efficacy, PA1010 may be used at a lower dose compared to TDF and TAF. In addition, the exposure levels of PMPA in the kidney in vivo produced from PA1010 and PA1007 were both significantly lower than those released from TAF and TDF (Table 5). In summary, PA1010 and PA1007 exhibited a higher ratio of liver to kidney than TAF and TDF at the same dose (FIGS. 4-7 and Table 5). The clinical nephrotoxicity was mainly caused by the enrichment of PMPA released from TDF and TAF in the kidney, which indicated that at the same dose, PA1010 and PA1007 may significantly alleviate the clinical nephrotoxicity caused by TDF and TAF.

TABLE 5

Exposure (area under the concentration-time curve (AUC0-t)(h * ng/g)) of the active molecule (PMPA) released from in vivo metabolism in plasma, liver and kidney after rats were administered with 30 mg/kg of PA1010, PA1007, TAF and TDF, respectively

| | PA1010 | PA1007 | TAF | TDF |
|---|---|---|---|---|
| Liver | 222692 | 76075 | 148407 | 78050 |
| Kidney | 234298 | 65393 | 297233 | 319562 |
| Plasma | 4332 | 1272 | 4892 | 3097 |
| Liver-kidney Ratio | 1.0 | 1.2 | 0.5 | 0.2 |
| Liver-plasma Ratio | 51.4 | 59.8 | 30.3 | 25.2 |

The above results indicated that due to a higher activity and liver-specific delivery, the compound of formula (I) or (III) of the present invention can be used for the treatment at a lower dose. Therefore, the compounds of the present invention had a higher safety or lower toxic and side effects, thereby greatly improving the clinical therapeutic index of PMPA.

All documents mentioned in the present application are hereby incorporated by reference as if each document is individually incorporated by reference. In addition, it should be understood that various modifications and changes may be made to the present invention without departing from the disclosure of the invention. These equivalents also fall within the scope defined by the appended claims.

What is claimed is:

1. A compound of the following structural formula or, a pharmaceutically acceptable salt, a hydrate or a solvate thereof:

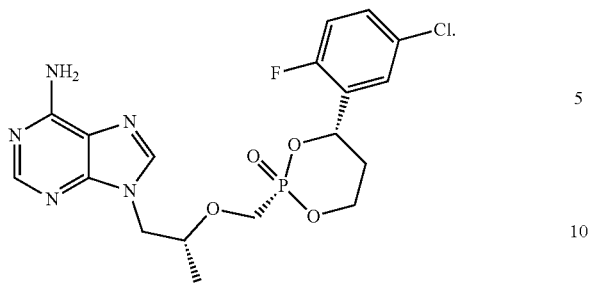

2. A pharmaceutical composition, comprising a therapeutically effective amount of the compound of claim 1 or, a pharmaceutically acceptable salt, a hydrate or a solvate thereof and a pharmaceutically acceptable auxiliary, diluent or carrier.

3. A method of treating hepatitis B virus (HBV) or hepatitis D virus (HDV) infections in a patient, comprising administering to the patient in need thereof an effective amount of a compound of claim 1, or a pharmaceutically acceptable salt, hydrate or a solvate thereof.

4. A method of treating hepatitis B virus (HBV) or hepatitis D virus (HDV) infections in a patient, comprising administering to the patient in need thereof an effective amount of a pharmaceutical composition comprising the compound of claim 1 or a pharmaceutically acceptable salt, hydrate or a solvate thereof.

* * * * *